(12) United States Patent
Kaseki et al.

(10) Patent No.: US 7,263,999 B2
(45) Date of Patent: Sep. 4, 2007

(54) RING FOR PREVENTING PROLAPSE OF UTERUS AND URINARY BLADDER AND RING FOR PREVENTING PROLAPSE OF UTERUS AND RECTUM

(75) Inventors: Hisayuki Kaseki, Kanagawa-ken (JP); Noboru Inagaki, Saitama-ken (JP); Tamotsu Inoue, Shizuoka-ken (JP)

(73) Assignee: Kabushiki Kaisha Kitazato Supply, Fujinomiya-Shi, Shizuoka-Ken (JP)

( * ) Notice: Subject to any disclaimer, the term of this patent is extended or adjusted under 35 U.S.C. 154(b) by 613 days.

(21) Appl. No.: 10/283,072

(22) Filed: Oct. 30, 2002

(65) Prior Publication Data
US 2004/0084054 A1    May 6, 2004

(51) Int. Cl.
*A61F 5/48* (2006.01)
(52) U.S. Cl. ............... 128/885; 128/834; 128/830
(58) Field of Classification Search ............ 128/830, 128/831, 832, 834, 839, 885
See application file for complete search history.

(56) References Cited

U.S. PATENT DOCUMENTS

| 4,516,570 | A | * | 5/1985 | Taban ................... 128/839 |
| 5,036,867 | A | | 8/1991 | Biswas |
| 5,386,836 | A | | 2/1995 | Biswas |
| 5,771,899 | A | * | 6/1998 | Martelly et al. ........... 128/830 |
| 6,436,428 | B1 | * | 8/2002 | Mahashabde et al. ...... 424/432 |
| 6,460,542 | B1 | * | 10/2002 | James ..................... 128/885 |
| 6,645,137 | B2 | * | 11/2003 | Ulmsten et al. ............ 600/29 |

* cited by examiner

*Primary Examiner*—Henry Bennett
*Assistant Examiner*—Camtu Nguyen
(74) *Attorney, Agent, or Firm*—Buchanan Ingersoll & Rooney PC

(57) ABSTRACT

A ring for preventing a prolapse of the uterus and the urinary bladder has an annular part and a flexible curved rod-shaped part whose one end and other end are so formed as to be connected to the annular part and whose intermediate portion interposed between the one end and the other end is so formed as to be disposed over a central region of an annular plane formed with the annular part The annular part has an open portion formed by a partial absence thereof.

9 Claims, 23 Drawing Sheets

RING FOR PREVENTING PROLAPSE OF UTERUS AND URINARY BLADDER AND RING FOR PREVENTING PROLAPSE OF UTERUS AND RECTUM

BACKGROUND OF THE INVENTION

The present invention relates to a ring for preventing a prolapse of the uterus and the urinary bladder. The present invention also relates to a ring for preventing a prolapse of the uterus and the rectum.

Many elderly women with prolapse of the uterus also have a complication of the urinary bladder. In according to the decrease in the force of the tissue and muscle supporting the uterus upward with the increase in age, the uterus may hang down from a fixed position. Hence a part of the uterus and a part of the wall of the urinary bladder on the periphery of the uterus may be exposed to the outside of a human body. This is the prolapse of the uterus and the urinary bladder. To treat the prolapse of the uterus and the urinary bladder, it is desirable to perform a vaginal hysterectomy, which is technically difficult to be performed. Moreover, elderly women have some complication of other diseases that would make the vaginoplasty riskier.

Elderly women also have a complication of the prolapse of the uterus and the rectum. To treat the prolapse of the uterus and the rectum, it is desirable to perform a vaginoplasty, which is technically difficult to be performed. Thus the vaginoplasty is hardly carried out That being the case, a conservative treatment without invasive operations should be required for both of the prolapse of the uterus and the urinary bladder. As a conservative treatment for the prolapse of the uterus, a method of inserting a ring pessary into the vagina to press the descensus upward is known. However, a simple round ring pessary, which just presses the cervix of the uterus upward, sometimes cause dyschezia because of pressing rectum wall together.

It is a first object of the present invention to provide a ring for preventing a prolapse of the uterus and the urinary bladder without causing the dyschezia by inserting the ring into the vagina.

That being the case, it is desirable to perform not an operation but a conservative treatment of both the prolapse of the uterus and the rectum. As a conservative treatment of the prolapse of the uterus, a method of inserting a ring pessary into the vagina to press the rectum with the uterus upward is known. However in this method, dyschezia may occur.

It is a second object of the present invention to provide a ring for preventing a prolapse of the uterus and the rectum without causing the dyschezia by inserting the ring into the vagina.

SUMMARY OF THE INVENTION

To achieve the first object, there is provided a ring, for preventing a prolapse of the uterus and the urinary bladder, having an annular part and a flexible curved rod-shaped part whose one end and other end are so formed as to be connected to the annular part and whose intermediate portion interposed between the one end and the other end is so formed as to be disposed over a central region of an annular plane formed with the annular part.

To achieve the first object, there is provided a ring, for preventing a prolapse of the uterus and the urinary bladder, having an annular part and a flexible curved rod-shaped part whose one end and other end integral with the one end are so formed as to be connected to the annular part and whose intermediate portion interposed between the one end and the other end is so formed as to be disposed over a central region of an annular plane formed with the annular part.

To achieve the first object, there is provided a ring, for preventing a prolapse of the uterus and the urinary bladder, having an annular part and a flexible curved rod-shaped part whose one end is connected to the annular part and whose other end is divided into at least two branches in such a way that the other end is disposed over a central region of an annular plane formed with the annular part.

To achieve the second object, there is provided a ring for preventing a prolapse of the uterus and the rectum including a flexible annular member having an open portion formed by a partial absence thereof. Both ends of the annular member forming the open portion are curved toward an inside of the annular member.

DETAILED DESCRIPTION OF THE PREFERRED EMBODIMENTS

The ring for preventing a prolapse of the uterus and the urinary bladder according to an embodiment of the present invention will be described in detail below with reference to the drawings.

A ring 1 of the present invention for preventing a prolapse of the uterus and the urinary bladder has an annular part 2 and a flexible curved rod-shaped part 3 whose one end and other end are so formed as to be connected to the annular part 2 and whose intermediate portion 3a interposed between the one end and the other end is so formed as to be disposed over a central region of an annular plane formed with the annular part 2.

Figure 1:
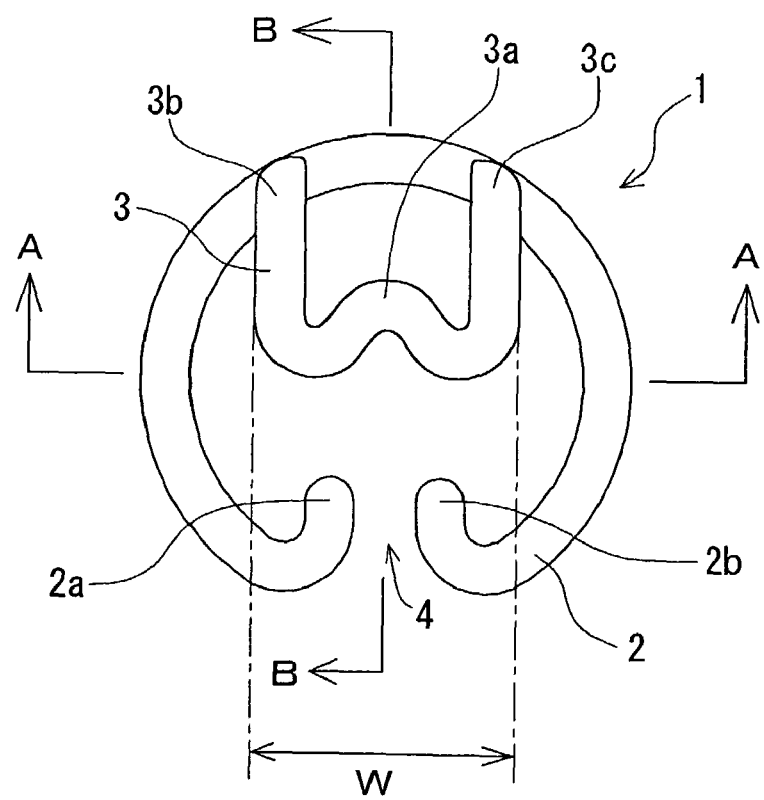
FIG. 1 is a front view showing a ring according to an embodiment of the present invention for preventing a prolapse of the uterus and the urinary bladder.

As shown in FIG. 1, the ring 1 of the embodiment has the annular part 2 for preventing the prolapse of the uterus, the flexible curved rod-shaped part 3 for preventing the prolapse of the urinary bladder, and an open portion 4, for preventing the prolapse of the rectum, formed by a partial absence of the annular part 2. Thus the ring 1 of the embodiment is of a type of preventing the prolapse of the uterus, the urinary bladder, and the rectum.

The ring 1 has the annular part 2 and the flexible curved rod-shaped part 3 connected thereto.

Figure 2:
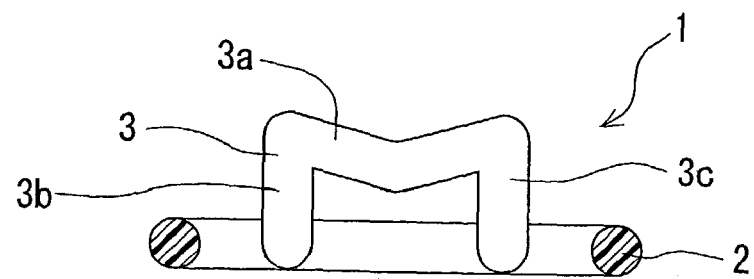
FIG. 2 is a sectional view taken along a line A—A of FIG. 1.
Figure 3:
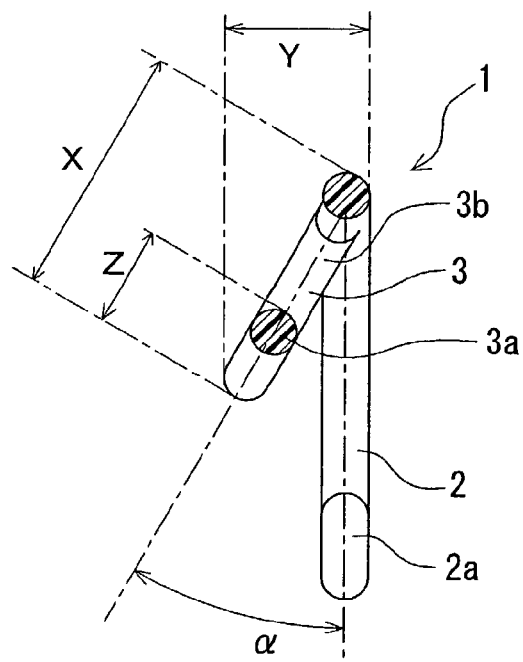
FIG. 3 is a sectional view taken along a line B—B of FIG. 1.

The annular part 2 is approximately a circular annular body and has the open portion 4 formed by a partial absence of the annular part 2. The provision of the open portion 4 makes it easy to insert the ring 1 into an organism and remove it therefrom, prevents the prolapse of the rectum without causing a dyschezia, and prevents a rotation of the ring 1 in the organism. Ends 2a and 2b of the annular part 2 forming the open portion 4 are curved toward the inside of the annular part 2. This configuration makes it possible to prevent the ends 2a and 2b of the annular part 2 from directly contacting the organism, namely, the uterus. The configuration of the annular part 2 is not limited to a circle but may be an ellipse or a deformed circle. As shown in FIGS. 2 and 3, the annular part 2 is formed as a curved column having a circular cross section. The annular part 2 may be a chamfered and curved polygonal pillar or a curved elliptical pillar. Although the size of the annular part 2 is varied according to the constitution of a patient, it is preferable that the annular part 2 has a diameter in the range of 40–120 mm. The thickness (diameter) of the entire annular part 2 does not necessarily have to be uniform. For example, a portion of the annular part 2 confronting the open portion 4 may be narrower than other portions thereof. This configuration allows an easier deformation of the annular part 2.

The thickness, or the diameter (maximum diameter) of the pillar constituting the annular part 2 is preferably in the range of 4 mm to 12 mm. The dimension of the open portion 4, namely, the dimension of the circular arc corresponding to the absent portion of the annular part 2 is favorably in the range of $\frac{1}{5}$ to $\frac{1}{30}$ of the circumference of the annular part 2 and more favorably in the range of $\frac{1}{8}$ to $\frac{1}{20}$ thereof. In the ring of the embodiment shown in FIG. 1 having the open portion 4, the distance between the ends 2a and 2b of the annular part 2 is preferably in the range of 10 to 30 mm. It is preferable that the ends 2a and 2b of the annular part 2 are curved toward the inside of the annular part 2 and approximately parallel with each other.

The curved rod-shaped part 3 is approximately w-shaped in such a way that its one end 3b and other end 3c are connected to the annular part 2. As shown in FIGS. 2 and 3, the intermediate portion 3a interposed between the one end and the other end is so formed as to be disposed over the central region of the annular plane formed with the annular part 2. The length X of the curved rod-shaped part 3 shown in FIG. 3 is preferably in the range of 20 mm to 50 mm. The height Y of the curved rod-shaped part 3 shown in FIG. 3 is preferably in the range of 20 mm to 40 mm. The angle a formed between the curved rod-shaped part and the annular part shown in FIG. 3 is favorably in the range of 30° to 150° and more favorably in the range of 30° to 60°. The width W of the curved rod-shaped part 3 shown in FIG. 1 is preferably in the range of 30 mm to 60 mm.

In the ring 1 of the embodiment, the intermediate portion 3a of the flexible curved rod-shaped part 3 is curved toward the annular part 2. The intermediate portion 3a of the flexible curved rod-shaped part 3 is curved toward an intermediate area between the one end and the other end thereof. Therefore the central portion of the flexible curved rod-shaped part 3 is prevented from strongly contacting the vaginal wall, and the entire flexible curved rod-shaped part 3 contacts the vaginal wall.

The curved distance Z of the intermediate portion 3a shown in FIG. 3 is preferably in the range of 10 mm–20 mm. As shown in FIG. 3, although the entire curved rod-shaped part 3 of the ring 1 is formed to be disposed on the same plane, the intermediate portion 3a thereof may be curved toward the center of the annular part 2. In this case, the entire curved rod-shaped part 3 is disposed not on the same plane but the intermediate portion 3a projects downward. The curved rod-shaped part 3 and the open portion 4 are formed at positions confronting each other.

As shown in FIGS. 1 through 3, the curved rod-shaped part 3 is formed as a curved column having a circular cross section. The curved rod-shaped part 3 may be a chamfered and curved polygonal pillar or a curved elliptical pillar. It is preferable that the pillar constituting the curved rod-shaped part 3 has a diameter (maximum diameter) of 4 mm–12 mm. The thickness (diameter) of the entire curved rod-shaped part 3 does not necessarily have to be uniform. For example, the intermediate portion 3a thereof may be narrower than other portions thereof.

The entire ring 1 of the embodiment is formed of a material flexible in some extent It is preferable that the material for the curved rod-shaped part 3 is more flexible than the material for the annular part 2.

As the material for the ring, the following substances can be used: semirigid materials such as polycarbonate, acrylic resin (for example, polyacrylate, polymethyl methacrylate, polyacrylamide, acrylonitrile-styrene copolymer, acrylonitrile-butadiene-styrene copolymer, polyester (for example, polyethylene terephthalate, polybutylene terephthalate), polyolefin (for example, polyethylene, polypropylene, ethylene-propylene copolymer, ethylene-vinyl acetate copolymer, mixture of polypropylene and polyethylene or polybutene), styrene resin (for example, polystyrene, methacrylate-styrene copolymer, methacrylate-butylene-styrene copolymer), polyamide (for example, 6 nylon, 66 nylon), and polysulfone; flexible materials such as synthetic rubber such as urethane rubber, silicone rubber, and butadiene rubber, natural rubber such as latex rubber, and thermoplastic materials such as olefin elastomer (for example, polyethylene elastomer, polypropylene elastomer), amide elastomer (for example, polyamide elastomer), styrene elastomer (for example, styrene-butadiene-styrene copolymer, styrene-isoprene-styrene copolymer, styrene-ethylene-butylene-styrene copolymer), polyurethane (for example, polyester polyurethane, polyether polyurethane), and urethane elastomer (for example, thermoplastic polyurethane, for example, thermoplastic polyether polyurethane and thermoplastic polyester polyurethane). Of these materials, it is preferable to use the thermoplastic materials. A resin that softens at a low temperature in the range of 50° C. to 100° C. is particularly preferable. Although the entire ring may be formed of the resin having a low softening point, it is indispensable that the annular part 2 is formed of the resin having a low softening point By using the resin having a low softening point and heating it to the above-described temperature, the annular part can be deformed into a configuration suitable for the configuration of the portion of a patient into which the ring is inserted. A deformed configuration can be maintained by cooling the resin. By doing so, it is possible to make removal of the ring from the inserted portion of the vaginal wall rare and reduce the degree of an unpleasant feeling of physical disorder at the time of its insertion into the vaginal wall. By using the resin having a low softening point and heating it to the above-described temperature, it is possible to arbitrarily alter the angle of the curved rod-shaped part 3 with respect to the annular part 2 as necessary.

The material for the annular part and the material for the curved rod-shaped part may be differentiated from each other. More specifically, the semirigid material may be used for the annular part and the flexible material may be used for the curved rod-shaped part In this case, both may be joined to each other with an adhesive agent, but it is preferable to integrate both with each other by carrying out a two-color molding method. As a combination of the materials when the two-color molding method is carried out, it is preferable that both are highly compatible with each other. More specifically, it is conceivable to select polyolefin as the semirigid material and polyolefin elastomer as the flexible material, ester resin as the semirigid material and polyester elastomer as the flexible material or styrene resin as the semirigid material and styrene elastomer as the flexible material.

The operation of the ring 1 is described below with reference to FIG. 44.

Figure 44:
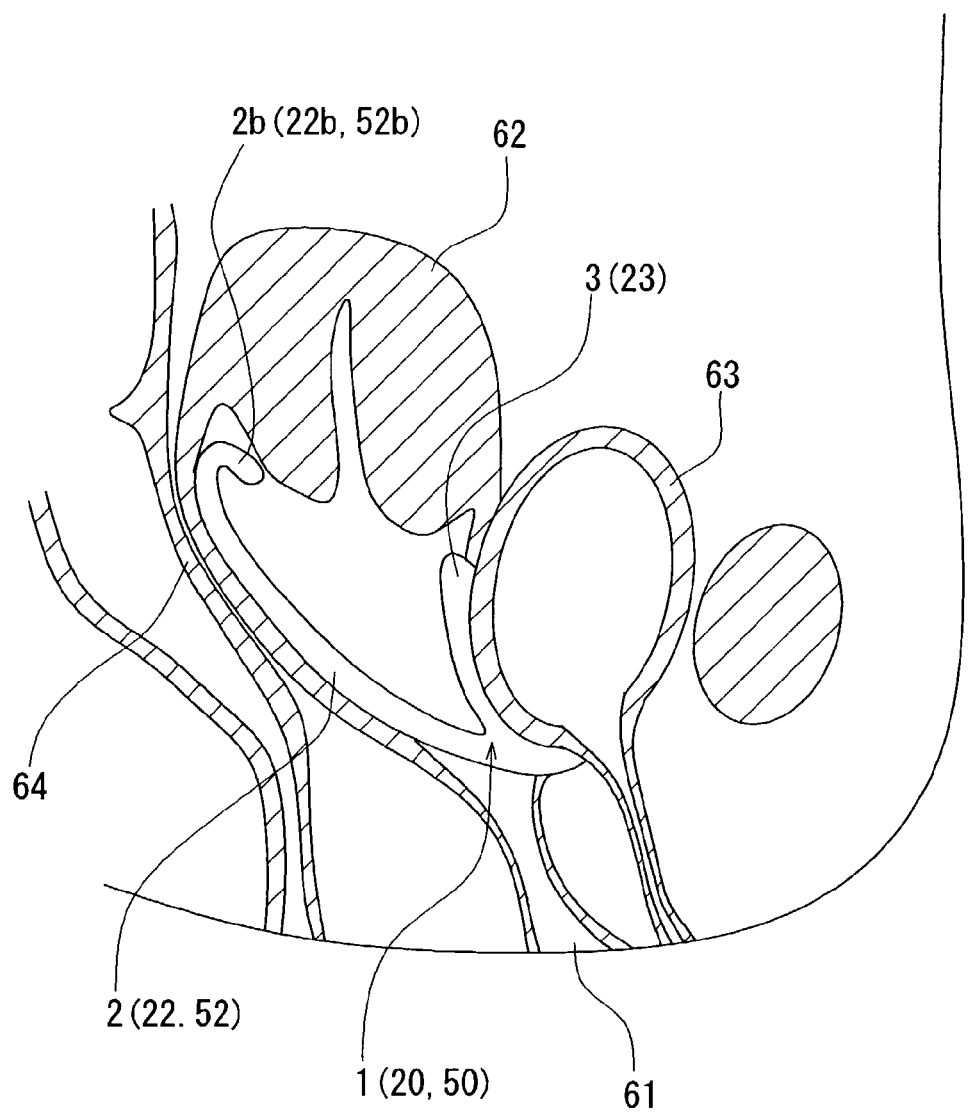
FIG. 44 is an explanatory view for explaining the operation of the ring of the present invention for preventing a prolapse of the uterus and the urinary bladder.

As shown in FIG. 44, the ring 1 is used by being inserted into a vagina 61. As shown in FIG. 44, the annular part 2 is inserted obliquely into the vagina 61 in such a way that the open portion 4 of the annular part 2 is disposed at a deep portion of the uterus 62, that the lower portion of the vagina is penetrated a little into the open portion 4, and that the lower portion of the urinary bladder 63 is disposed on the curved rod-shaped part 3. In this state, the uterus 62 is pressed upward by the annular part 2, and the urinary bladder 63 is supported by the curved rod-shaped part 3 from below, and the rectal wall 64 is pressed upward by the annular part 2 through the vaginal wall. Thereby the symptoms of the prolapse of the uterus, the urinary bladder, and the rectum are reduced. Since the annular part 2 has the open portion, i.e., since it has a portion that does not press the rectum, it is possible to reduce occurrence of dyschezia.

Figure 4:
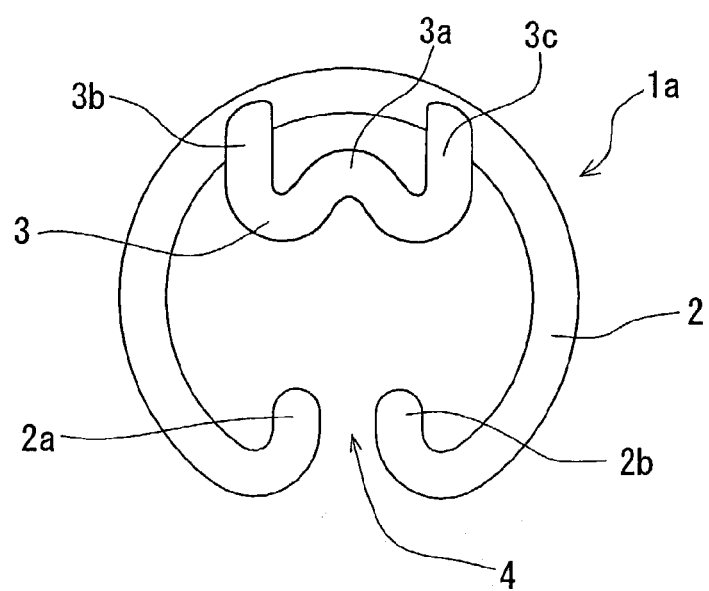
FIG. 4 is a front view showing a ring according to another embodiment of the present invention for preventing a prolapse of the uterus and the urinary bladder.

Like a ring 1a shown in FIG. 4, the curved rod-shaped part 3 may be shorter than that shown in FIGS. 1 through 3. In this case, with reference to FIG. 3, the length X of the curved rod-shaped part is preferably in the range of 20 mm to 50 mm, and the height Y thereof is preferably in the range of 20 mm to 40 mm. The other specifications of the ring 1a is the same as those of the ring 1.

Figure 5:
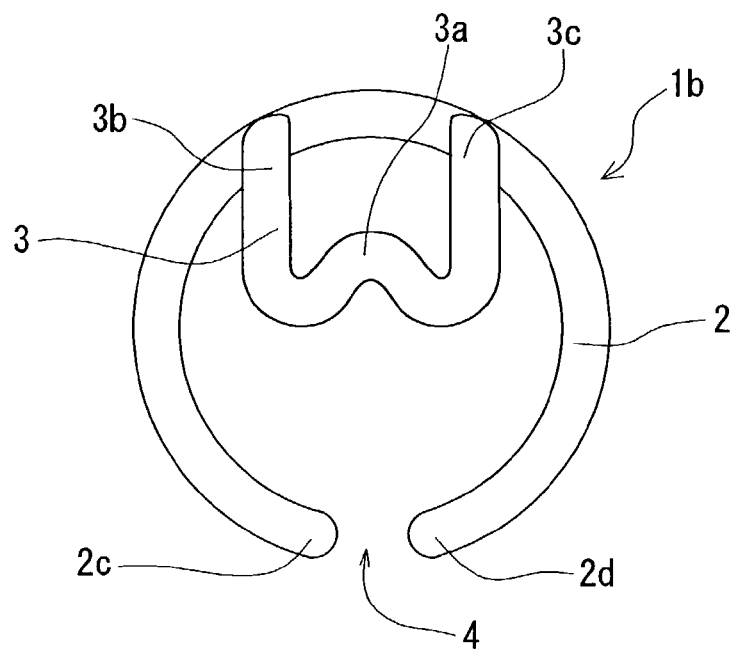
FIG. 5 is a front view showing a ring according to another embodiment of the present invention for preventing a prolapse of the uterus and the urinary bladder.

Like a ring 1b shown in FIG. 5, ends 2c and 2d of the annular part 2 at its open portion may confront each other.

In the ring 1d, the dimension of the open portion 4, namely, the dimension of the circular arc corresponding to the absent portion of the annular part 2 is favorably in the range of 1/5–1/30 of the circumference of the annular part 2 and more favorably in the range of 1/9–1/20 thereof. The distance between the ends 2c and 2d of the annular part 2 is preferably in the range of 10 mm–30 mm. The other specifications of the ring 1b are the same as those of the ring 1.

Figure 6:
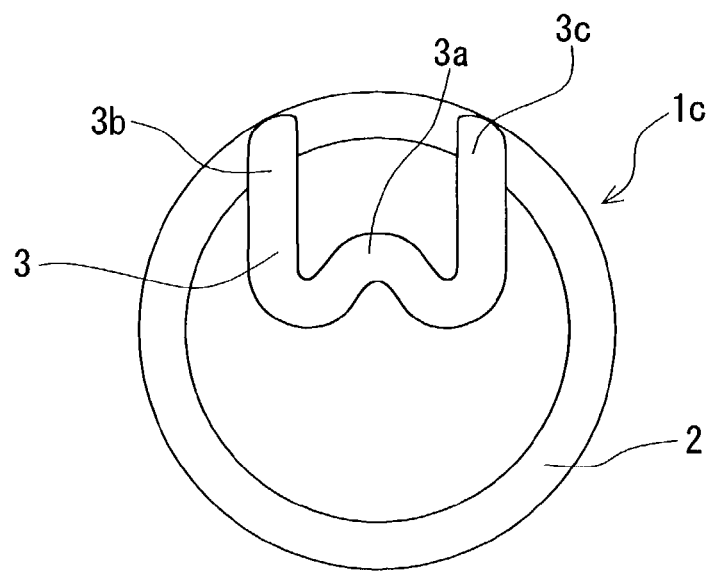
FIG. 6 is a front view showing a ring according to another embodiment of the present invention for preventing a prolapse of the uterus and the urinary bladder.

Like a ring 1c shown in FIG. 6, the annular part 2 may not be provided with the open portion. The ring 1c is effective for a patient having the symptoms of the prolapse of the uterus and the urinary bladder but not the symptoms of the rectum. The other specifications of the ring 1c are the same as those of the ring 1.

Figure 27:
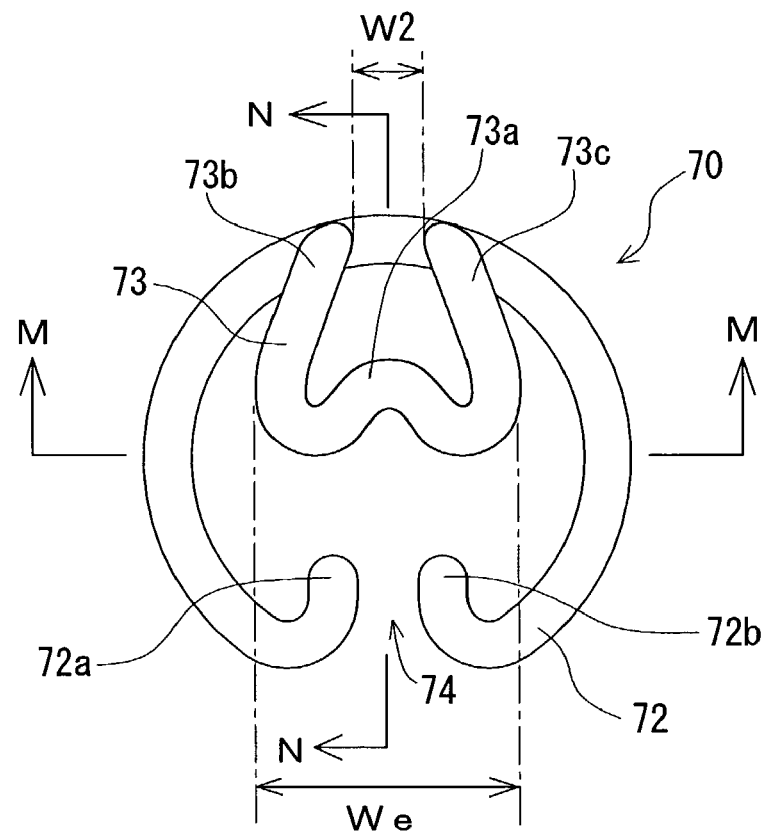
FIG. 27 is a front view showing a ring according to another embodiment of the present invention for preventing a prolapse of the uterus and the urinary bladder.
Figure 28:
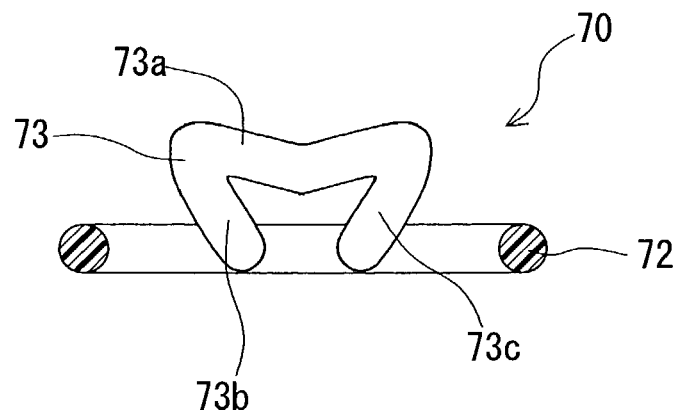
FIG. 28 is a sectional view taken along a line M—M of FIG. 27.
Figure 29:
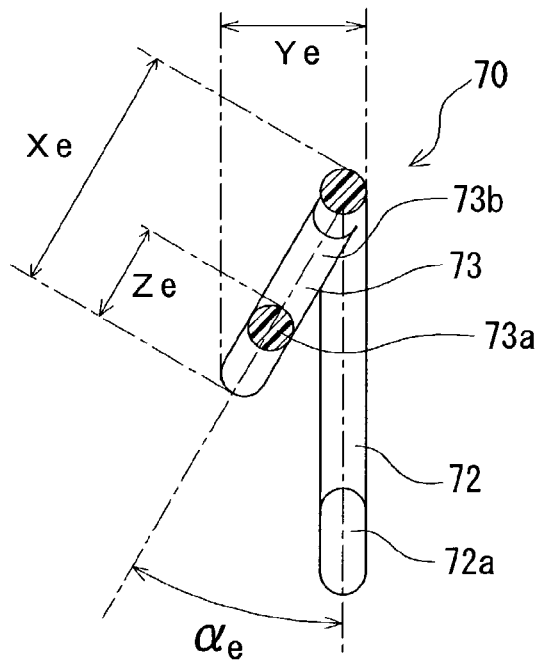
FIG. 29 is a sectional view taken along a line N—N of FIG. 27.

Like a ring 70 for preventing a prolapse of the uterus and the urinary bladder shown in FIGS. 27, 28, and 29, a curved rod-shaped part 73 is so formed that one end 73b thereof and the other end 73c thereof are connected to the annular part 72 and that the distance between the one end 73b and the other end 73c is shorter than the distance between the one end 3b and the other end 3c of the curved rod-shaped part 3 of the ring 1 shown in FIG. 1. In other words, the curved rod-shaped part 73 may have a deformed w-shaped configuration in which the distance between the one end 73b and the other end 73c is short.

FIG. 27 is a front view showing a ring for preventing the prolapse of the uterus and the urinary bladder according to another embodiment of the present invention. FIG. 28 is a sectional view taken along a line M—M of FIG. 27. FIG. 29 is a sectional view taken along a line N—N of FIG. 27.

As shown in FIGS. 28 and 29, an central portion 73a of the curved rod-shaped part 73 interposed between the one end thereof and the other end thereof is so formed as to be disposed over a central region of an annular plane formed with an annular part 72. The length Xe of the curved rod-shaped part 73 shown in FIG. 29 is preferably in the range of 20 mm to 50 mm. The height Ye of the curved rod-shaped part 73 shown in FIG. 29 is preferably in the range of 20 mm to 40 mm. The angle αe formed between the curved rod-shaped part and the annular part shown in FIG. 29 is favorably in the range of 30° to 150° and more favorably in the range of 30° to 60°. The width We of the curved rod-shaped part shown in FIG. 27 is preferably in the range of 30 mm to 60 mm. The width W2 between the one end of the curved rod-shaped part and the other end thereof shown in FIG. 27 is preferably in the range of 5 mm to 30 mm.

In the ring 70 of the embodiment, an intermediate portion of the flexible curved rod-shaped part 73 is curved toward the annular part 72. The intermediate portion of the flexible curved rod-shaped part 73 is curved toward an intermediate area between the one end and the other end thereof. Therefore the central portion of the flexible curved rod-shaped part 73 is prevented from strongly contacting an organism, and the entire flexible curved rod-shaped part 73 contacts the organism.

The curved distance Ze of the central portion 73a shown in FIG. 29 is preferably in the range of 10 mm to 20 mm. As shown in FIG. 29, although the entire curved rod-shaped part 73 of the ring 70 is formed to be disposed on the same plane, the central portion 73a thereof may be curved toward the center of the annular part 72. In this case, the entire curved rod-shaped part 73 is not disposed on the same plane but the central portion 73a projects downward. The curved rod-shaped part 73 and an open portion 74 are so formed as to confront each other.

As shown in FIGS. 27 through 29, the curved rod-shaped part 73 is formed as a curved column having a circular cross section. The curved rod-shaped part 73 may be a chamfered and curved polygonal pillar or a curved elliptical pillar. It is preferable that the pillar constituting the curved rod-shaped part 73 has a diameter (maximum diameter) of 4 mm to 12 mm. The thickness (diameter) of the entire curved rod-shaped part 73 does not necessarily have to be uniform. For example, the central portion 73a may be narrower than other portions thereof.

The entire ring 70 of the embodiment is formed of a material flexible in some extent It is preferable that the material for the curved rod-shaped part 73 is more flexible than the material for the annular part 72.

Figure 30:
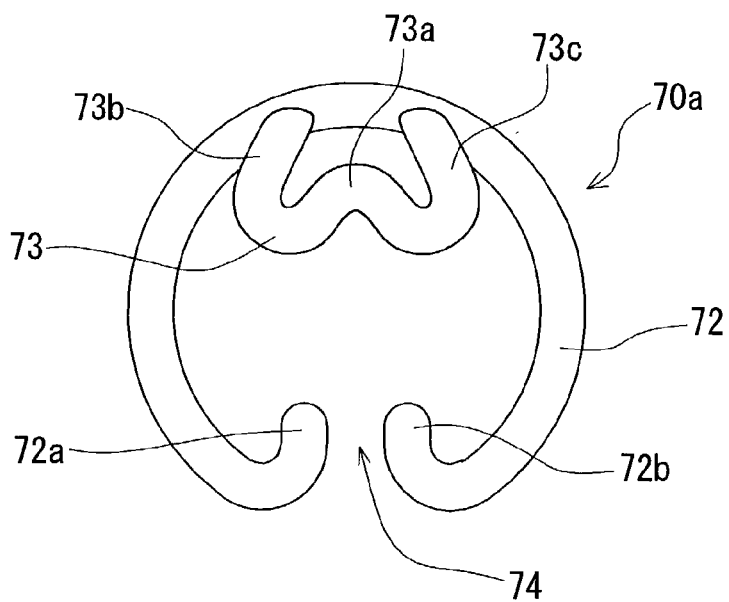
FIG. 30 is a front view showing a ring according to another embodiment of the present invention for preventing a prolapse of the uterus and the urinary bladder.

Like a ring 70a shown in FIG. 30, its curved rod-shaped part 73 may be shorter than that of the ring 70 shown in FIGS. 27 through 29. In this case, with reference to FIG. 29, the length Xe of the curved rod-shaped part is preferably in the range of 20 mm to 50 mm, and the height Ye thereof is preferably in the range of 20 mm to 40 mm. The other specifications of the ring 70a are the same as those of the ring 70.

Figure 31:
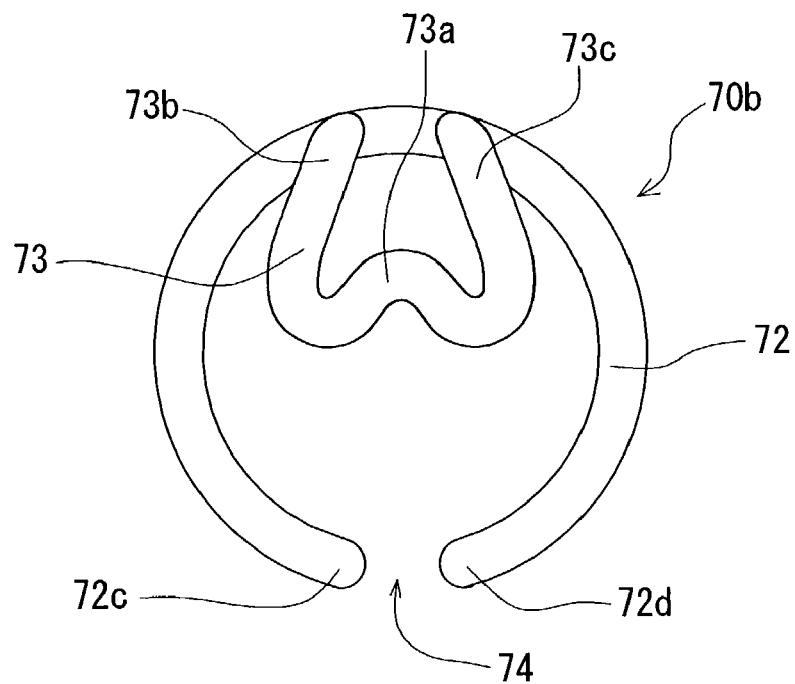
FIG. 31 is a front view showing a ring according to another embodiment of the present invention for preventing a prolapse of the uterus and the urinary bladder.

Like a ring 70b shown in FIG. 31, ends 72c and 72d of the annular part 72 at its open portion may confront each other. In the ring 70b, the dimension of the open portion 74, namely, the dimension of the circular arc corresponding to the absent portion of the annular part 72 is favorably in the range of 1/5 to 1/30 of the circumference of the annular part 72 and more favorably in the range of 1/9 to 1/20 thereof. The distance between the ends 72c and 72d of the annular part 72 is preferably in the range of 10 mm to 30 mm. The other specifications of the ring 70b are the same as those of the ring 70 shown in FIGS. 27 through 29.

Figure 32:
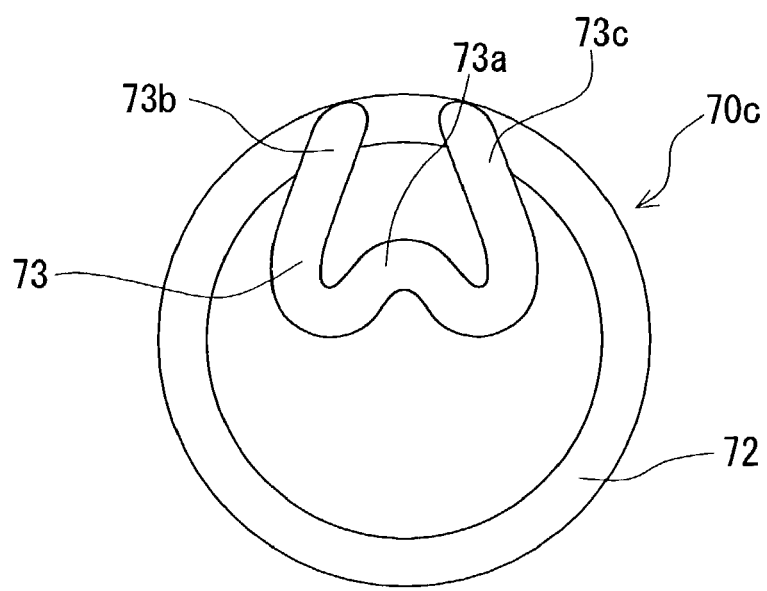
FIG. 32 is a front view showing a ring according to another embodiment of the present invention for preventing a prolapse of the uterus and the urinary bladder.

Like a ring 70c shown in FIG. 32, the annular part 72 may not be provided with the open portion. The ring 70c is effective for a patient having the symptoms of the prolapse of the uterus and the urinary bladder but not the symptoms of the rectum. The other specifications of the ring 70c are the same as those of the ring 70 shown in FIGS. 27 and 29.

A ring 10, shown in FIGS. 7 through 9, for preventing a prolapse of the uterus and the urinary bladder according to another embodiment of the present invention will be described below. The ring 10 is the same as the ring 1 except that the curved rod-shaped part of the ring 10 is different from that of the ring 1.

Figure 7:
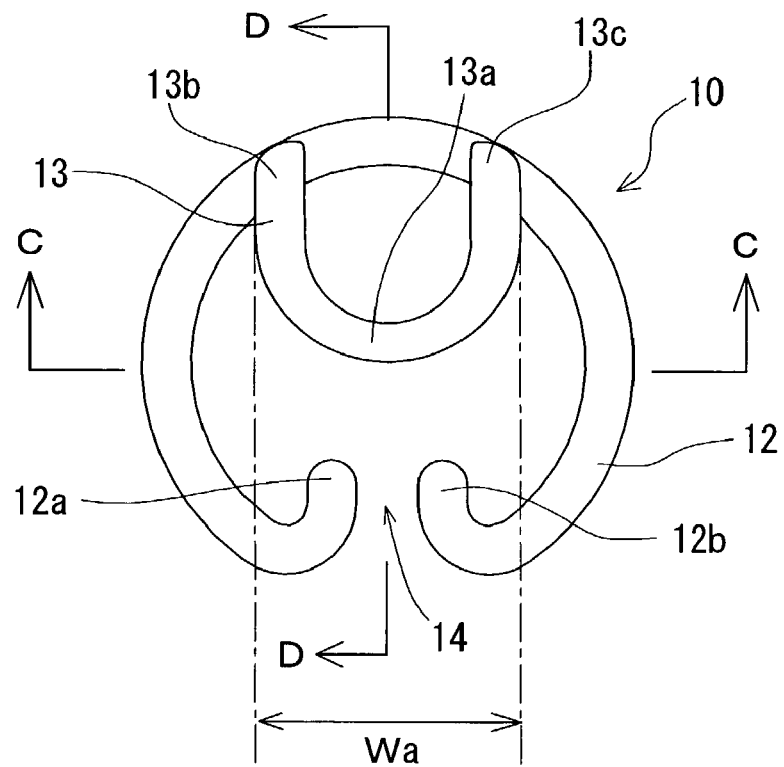
FIG. 7 is a front view showing a ring according to another embodiment of the present invention for preventing a prolapse of the uterus and the urinary bladder.

FIG. 7 is a front view showing the ring for preventing the prolapse of the uterus and the urinary bladder according to another embodiment of the present invention. FIG. 8 is a sectional view taken along a line C—C of FIG. 7. FIG. 9 is a sectional view taken along a line D—D of FIG. 7.

In the ring 10 of this embodiment a curved rod-shaped part 13 is approximately U-shaped in such a way that one end 13b thereof and the other end 13c thereof are connected to the annular part 12. As shown in FIGS. 8 and 9, an intermediate portion 13a of the curved rod-shaped part 13 is smaller than the other portion in its diameter. Thereby the central portion 13a of the curved rod-shaped part 13 is more flexible than the other portions thereof. Similarly to the ring 1, the curved rod-shaped part 13 is so formed as to dispose over a central region of an annular plane formed with the annular part 12.

Figure 9:
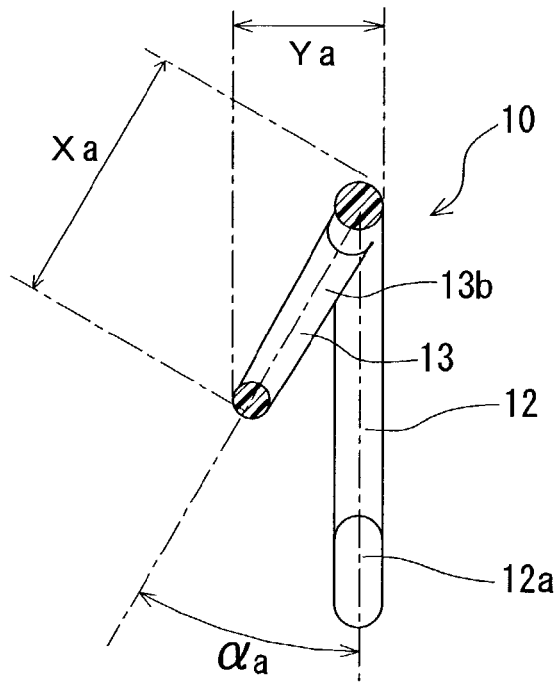
FIG. 9 is a sectional view taken along a line D—D of FIG. 7.

The length Xa of the curved rod-shaped part 13 shown in FIG. 9 is preferably in the range of 20 mm to 50 mm. The height Ya of the curved rod-shaped part 13 shown in FIG. 9 is preferably in the range of 20 mm to 40 mm. The angle αa formed between the curved rod-shaped part and the annular part shown in FIG. 9 is favorably in the range of 45° to 80°.

The width Wa of the curved rod-shaped part shown in FIG. 7 is preferably in the range of 30 mm to 50 mm. As shown in FIG. 9, although the entire curved rod-shaped part 13 of the ring 10 is formed to be disposed on the same plane, the central portion 13a thereof may be curved toward the center of the annular part 12. In this case, the entire curved rod-shaped part 13 is not disposed on the same plane but the central portion 13a projects downward. The curved rod-shaped part 13 and an open portion 14 are so formed as to confront each other.

Figure 8:
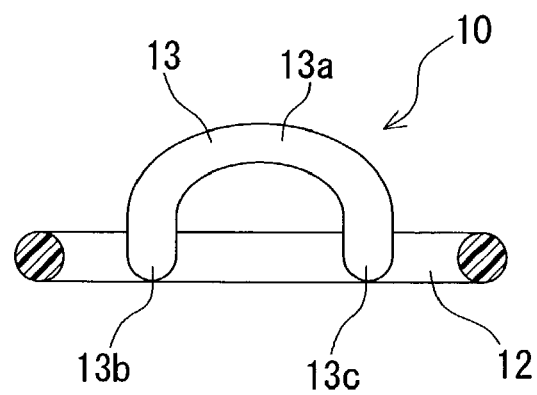
FIG. 8 is a sectional view taken along a line C—C of FIG. 7.

As shown in FIGS. 7 through 9, the curved rod-shaped part 13 is formed as a curved column having a circular cross section. The curved rod-shaped part 13 may be a chamfered and curved polygonal pillar or a curved elliptical pillar. It is preferable that the pillar constituting the curved rod-shaped part 13 has a diameter (maximum diameter) of 4 mm to 12 mm. The thickness of the curved rod-shaped part 13 is nonuniform. The central portion of the intermediate portion 13a is narrowest of all the portions of the curved rod-shaped part 13. The thickness of the central portion of the intermediate portion 13a is preferably in the range of 3 mm to 10 mm in its diameter (maximum diameter).

Figure 10:
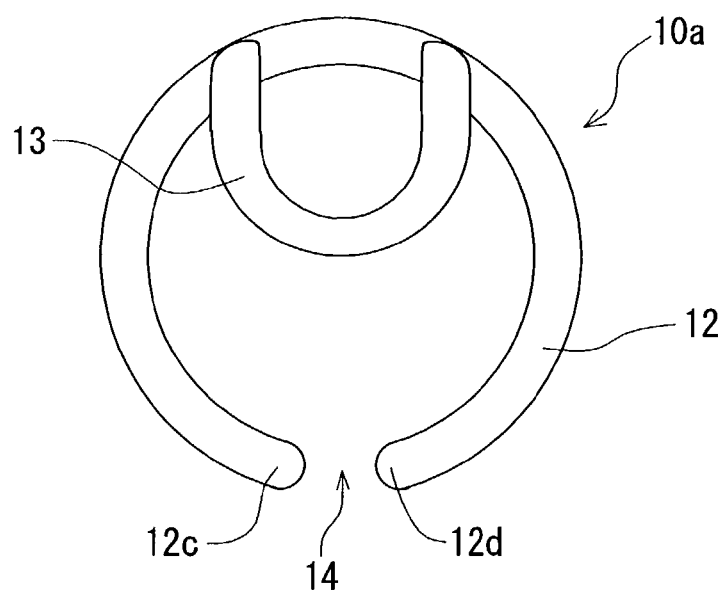
FIG. 10 is a front view showing a ring according to another embodiment of the present invention for preventing a prolapse of the uterus and the urinary bladder.

Like a ring 10a shown in FIG. 10, ends 12c and 12d of the annular part 12 at its open portion may confront each other. In the ring 10a, the dimension of the open portion 14, namely, the dimension of the circular arc corresponding to the absent portion of the annular part 12 is favorably in the range of ⅕ to ⅟₃₀ of the circumference of the annular part 12. The distance between the ends 12c and 12d of the annular part 12 is preferably in the range of 10 mm to 30 mm. The specifications of the curved rod-shaped part 13 are the same as those of the ring 10. The size of the annular part and the material for the ring 10a are also the same as those of the ring 1.

Figure 11:
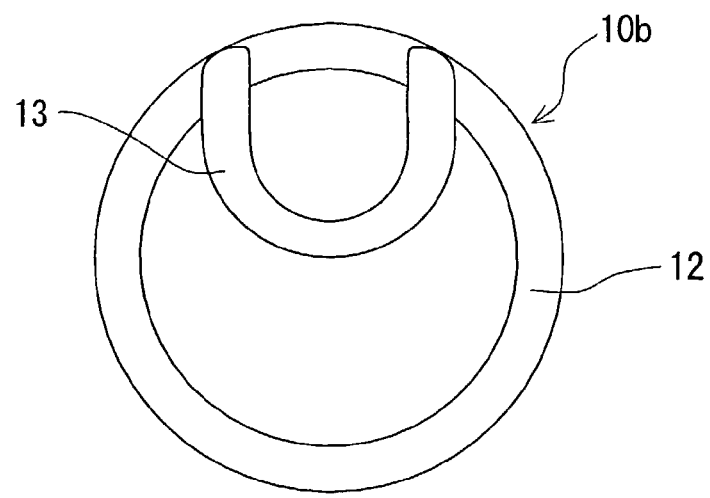
FIG. 11 is a front view showing a ring according to another embodiment of the present invention for preventing a prolapse of the uterus and the urinary bladder.

Like a ring 10b shown in FIG. 11, the annular part 12 may not be provided with the open portion. The ring 10b is effective for a patient having the symptoms of the prolapse of the uterus and the urinary bladder but not the symptoms of the rectum. The specifications of the curved rod-shaped part 13 are the same as those of the ring 10. The size of the annular part and the material for the ring 10b are also the same as those of the ring 1.

A ring of another type for preventing a prolapse of the uterus and the urinary bladder according to the present invention will be described below.

Figure 12:
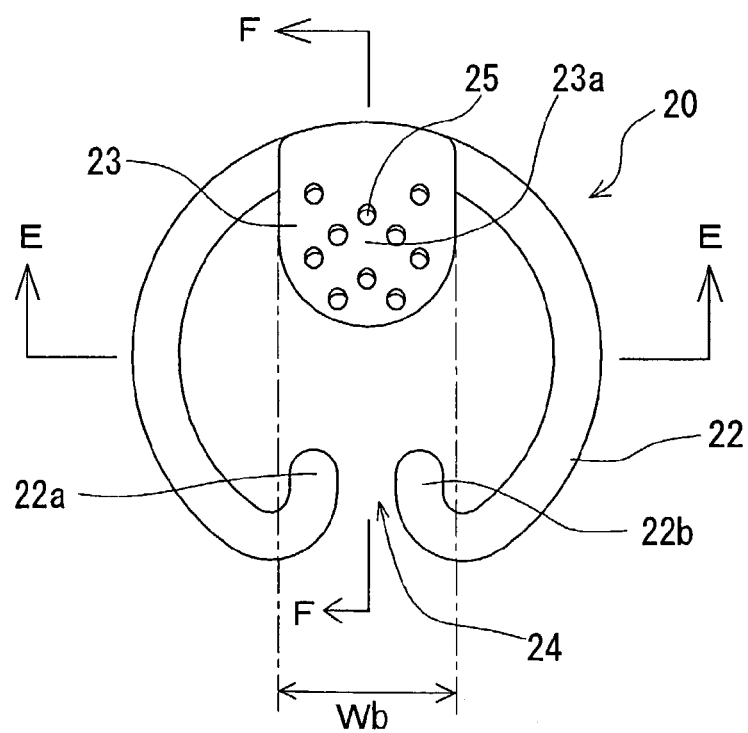
FIG. 12 is a front view showing a ring according to another embodiment of the present invention for preventing a prolapse of the uterus and the urinary bladder.
Figure 13:
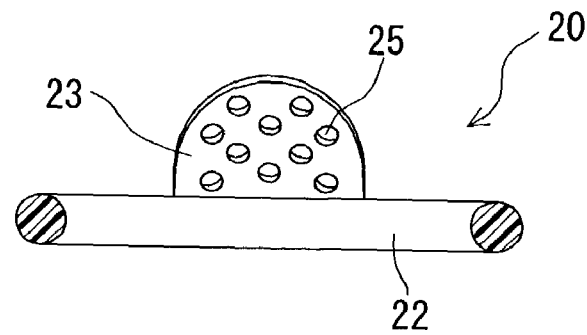
FIG. 13 is a sectional view taken along a line E—E of FIG. 12.
Figure 14:
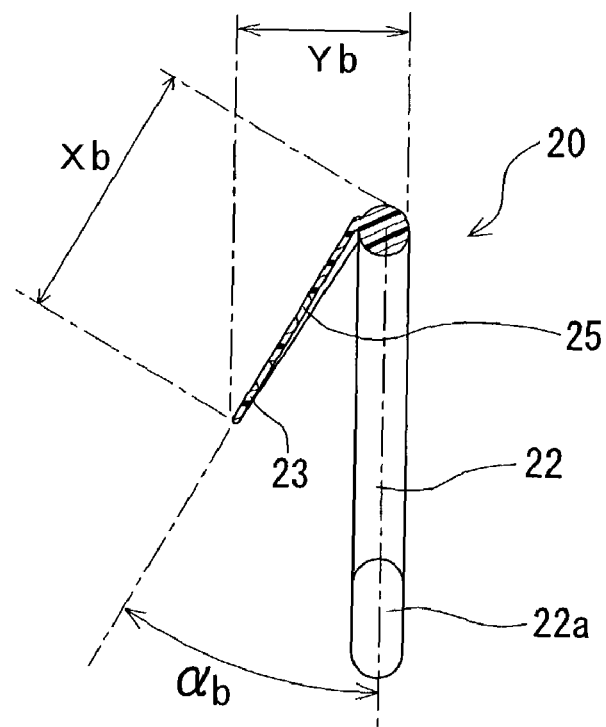
FIG. 14 is a sectional view taken along a line F—F of FIG. 12.

FIG. 12 is a front view showing a ring for preventing the prolapse of the uterus and the urinary bladder according to another embodiment of the present invention. FIG. 13 is a sectional view taken along a line E—E of FIG. 12. FIG. 14 is a sectional view taken along a line F—F of FIG. 12.

A ring 20 of the present invention for preventing the prolapse of the uterus and the urinary bladder has an annular part 22 and a tongue-shaped flexible flat plate part 23 formed on the annular part 22 in such a way that the tongue-shaped flexible flat plate part 23 is disposed over a central region of an annular plane formed with the annular part 22.

As shown in FIG. 12, the ring 20 of the embodiment has the annular part 22 for preventing the prolapse of the uterus, the tongue-shaped flexible flat plate part 23 for preventing the prolapse of the urinary bladder, and the open portion 24, for preventing the prolapse of the rectum, formed by a partial absence of the annular part 22. Thus the ring 20 of the embodiment is of a type of preventing the prolapse of the uterus, the urinary bladder, and the rectum.

The ring 20 has the annular part 22 and the tongue-shaped flexible flat plate part 23 connected thereto.

The annular part 22 is approximately a circular annular body and has an open portion 24 formed by a partial absence of the annular part 22. The provision of the open portion 24 makes it easy to insert the ring 20 into an organism and remove it therefrom, prevents the prolapse of the rectum without causing a dyschezia, and prevents a rotation of the ring 20 in the organism. Ends 22a and 22b of the annular part 22 forming the open portion 24 are curved toward the inside of the annular part 22. Thus it is possible to prevent the ends 22a and 22b of the annular part 22 from directly contacting the organism, namely, the uterus. The configuration of the annular part 22 is not limited to a circle but may be an ellipse or a deformed circle. As shown in FIGS. 13 and 14, the annular part 22 is formed as a curved column having a circular cross section. The annular part 22 may be a chamfered and curved polygonal pillar or a curved elliptical pillar. Although the size of the annular part 22 is varied according to the constitution of a patient, it is preferable that the annular part 22 has a diameter in the range of 40 mm to 120 mm. It is preferable that the pillar constituting the annular part 22 has a diameter (maximum diameter) of 4 mm to 12 mm. The thickness (diameter) of the entire annular part 22 does not necessarily have to be uniform. For example, a portion of the annular part 22 confronting the open portion 24 may be narrower than other portions thereof. This configuration allows an easier deformation of the annular part 22.

The dimension of the open portion 24, namely, the dimension of the circular arc corresponding to the absent portion of the annular part 22 is favorably in the range of ⅕ to ⅟₃₀ of the circumference of the annular part 22. In the embodiment shown in FIG. 12 in which the ring 20 has the open portion 24, the distance between the ends 22a and 22b of the annular part 22 is preferably in the range of 10 mm to 30 mm. It is preferable that the ends 22a and 22b of the annular part 22 are curved toward the inside of the annular part 22 and approximately parallel with each other.

The flexible flat plate part 23 is tongue-shaped in such a way that its one end is connected to the annular part 22. As shown in FIGS. 13 and 14, the flexible flat plate part 23 is so formed as to be disposed over the central region of the annular plane formed with the annular part 22. The length Xb of the flexible flat plate part shown in FIG. 14 is preferably in the range of 20 mm to 50 mm. The height Yb of the flexible flat plate part 23 shown in FIG. 14 is preferably in the range of 20 mm to 40 mm. The angle αb formed between the flexible flat plate part and the annular part shown in FIG. 14 is favorably in the range of 45° to 80°. The width Wb of the flexible flat plate part shown in FIG. 12 is preferably in the range of 30 mm to 50 mm.

The leading end of the flexible flat plate part 23 is tongue-shaped or curved like a circular arc. The flexible flat plate part 23 has a plurality of openings 25 penetrating therethrough. The opening 25 prevents an excessive contact between the flexible flat plate part 23 and the organism and also prevents a metabolite from depositing between the flexible flat plate part 23 and the organism. The dimension (diameter) of the opening 25 is preferably in the range of 1 mm to 4 mm. The number of the openings 25 is preferably in the range of one to three/$cm^2$.

As shown in FIG. 14, although the entire flexible flat plate part 23 of the ring is formed to be disposed on the same plane, [an intermediate portion] a central portion 23a of the flexible flat plate part 23 may be curved toward the center of the annular part 22. In this case, the entire flexible flat plate part 23 is not disposed on the same plane but the central portion 23a projects downward. The flexible flat plate part 23 and the open portion 24 are so formed as to confront each other.

As shown in FIGS. 12 through 14, the flexible flat plate part 23 is formed of a thin plate having a uniform thickness. The thickness of the flexible flat plate part is preferably in the range of 3 mm to 8 mm.

The entire ring 20 of the embodiment is formed of a material flexible in some extent It is preferable that the material for the flexible flat plate part 23 is more flexible than the material for the annular part 22.

As the material for the ring, the following substances can be used: semirigid materials such as polycarbonate, acrylic resin (for example, polyacrylate, polymethyl methacrylate, polyacrylamide, acrylonitrile-styrene copolymer, acrylonitrile-butadiene-styrene copolymer, polyester (for example, polyethylene terephthalate, polybutylene terephthalate), polyolefin (for example, polyethylene, polypropylene, ethylene-propylene copolymer, ethylene-vinyl acetate copolymer, mixture of polypropylene and polyethylene or polybutene), styrene resin (for example, polystyrene, methacrylate-styrene copolymer, methacrylate-butylene-styrene copolymer), polyamide (for example, 6 nylon, 66 nylon), and polysulfone; flexible materals such as synthetic rubber such as urethane rubber, silicone rubber, and butadiene rubber, natural rubber such as latex rubber, and thermoplastic materials such as olefin elastomer (for example, polyethylene elastomer, polypropylene elastomer), amide elastomer (for example, polyamide elastomer), styrene elastomer (for example, styrene-butadiene-styrene copolymer, styrene-isoprene-styrene copolymer, styrene-ethylene-butylene-styrene copolymer), polyurethane (for example, polyester polyurethane, polyether polyurethane), and urethane elastomer (for example, thermoplastic polyurethane, for example, thermoplastic polyether polyurethane and thermoplastic polyester polyurethane). Of these materials, it is preferable to use the thermoplastic materials. A resin that softens at a low temperature in the range of 50° C. to 100° C. is particularly preferable. Although the entire ring may be formed of the resin having a low softening point, it is indispensable that the annular part 22 is formed of the resin having a low softening point By using the resin having a low softening point and heating it to the above-described temperature, the annular part can be deformed into a configuration suitable for the configuration of the portion of a patient into which the ring is inserted. A deformed configuration can be maintained by cooling the resin. By doing so, it is possible to make removal of the ring from the inserted portion of the organism rare and reduce the degree of an unpleasant feeling of physical disorder at the time of its insertion into the organism. By using the resin having a low softening point and heating it to the above-described temperature, it is possible to arbitrarily alter the angle of the curved rod-shaped part with respect to the annular part as necessary.

The material for the annular part and the material for the flexible flat plate member may be differentiated from each other. More specifically, the semirigid material may be used for the annular part and the flexible material may be used for the flexible flat plate member. In this case, both may be joined to each other with an adhesive agent, but it is preferable to integrate both with each other by carrying out a two-color molding method. As a combination of the materials when the two-color molding method is carried out, it is preferable that both are highly compatible with each other. More specifically, it is conceivable to select polyolefin as the semirigid material and polyolefin elastomer as the flexible material, ester resin as the semirigid material and polyester elastomer as the flexible material or styrene resin as the semirigid material and styrene elastomer as the flexible material.

The operation of the ring 20 is described below with reference to FIG. 44.

As shown in FIG. 44, the ring 20 is used by being inserted into a vagina 61. As shown in FIG. 44, the annular part 22 is inserted obliquely into the vagina 61 in such a way that the open portion 24 of the annular part 22 is disposed at a deep portion of the uterus 62, that the lower portion of the vagina is penetrated a little into the open portion 24, and that the lower portion of the urinary bladder 63 is disposed on the flexible flat plate part 23. In this state, the uterus 62 is pressed upward by the annular part 22, and the urinary bladder 63 is supported by the flexible flat plate part 23 from below, and the rectal wall 64 is pressed upward by the annular part 22 through the vaginal wall. Thereby the symptoms of the prolapse of the uterus, the urinary bladder, and the rectum are reduced. Since the annular part 22 has the open portion, i.e., since it has a portion that does not press the rectum, it is possible to reduce occurrence of dyschezia.

Figure 15:
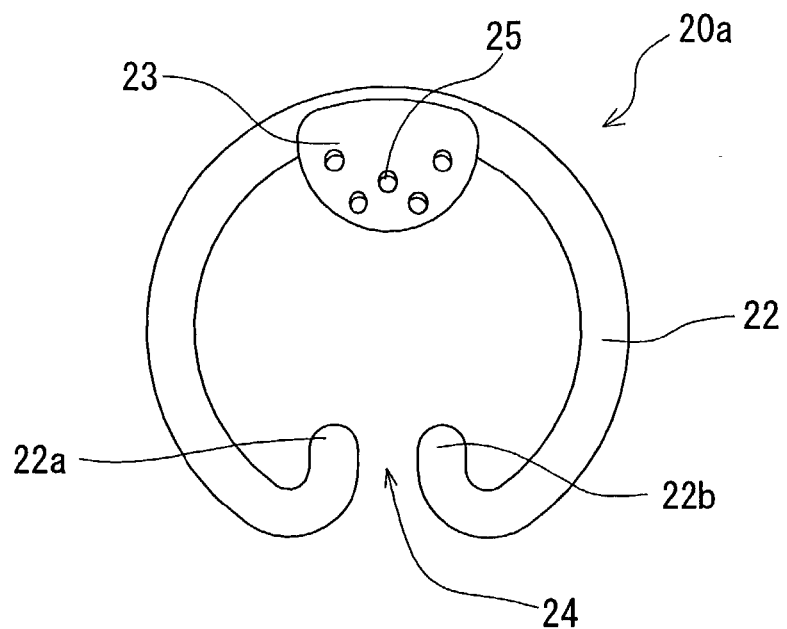
FIG. 15 is a front view showing a ring according to another embodiment of the present invention for preventing a prolapse of the uterus and the urinary bladder.

Like a ring 20a shown in FIG. 15, the flexible flat plate part 23 may be shorter than that shown in FIGS. 12 through 14. In this case, with reference to FIG. 14, the length Xb of the flexible flat plate part is preferably in the range of 20 mm to 50 mm, and the height Yb thereof is preferably in the range of 20 mm to 40 mm. The other specifications of the ring 20a are the same as those of the ring 20.

Figure 16:
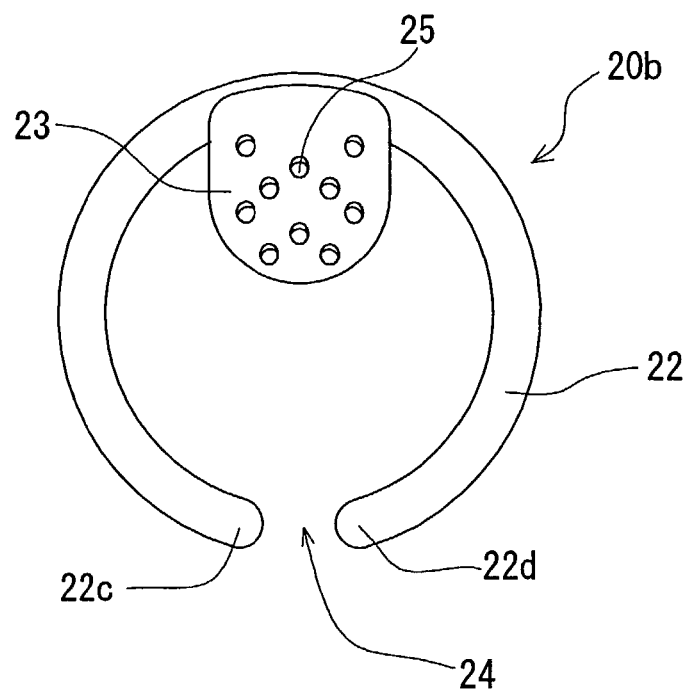
FIG. 16 is a front view showing a ring according to another embodiment of the present invention for preventing a prolapse of the uterus and the urinary bladder.

Like a ring 20b shown in FIG. 16, ends 22c and 22d of the annular part 22 at its open portion may confront each other. In the ring 20b, the dimension of the open portion 24, namely, the dimension of the circular arc corresponding to the absent portion of the annular part 22 is favorably in the range of ⅕ to ¹⁄₃₀ of the circumference of the annular part 2 and more favorably in the range of ⅛ to ¹⁄₂₀ thereof. The distance between the ends 22c and 22d of the annular part 22 is preferably in the range of 10 mm to 30 mm. The other specifications of the ring 20b are the same as those of the ring 20.

Figure 17:
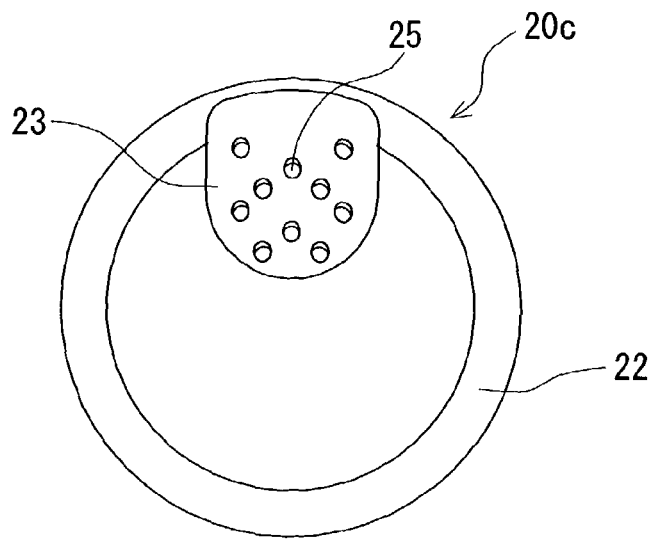
FIG. 17 is a front view showing a ring according to another embodiment of the present invention for preventing a prolapse of the uterus and the urinary bladder.

Like a ring 20c shown in FIG. 17, the annular part 22 may not be provided with the open portion. The ring 20c is effective for a patient having the symptoms of the prolapse of the uterus and the urinary bladder but not the symptoms of the rectum. The other specifications of the ring 20c are the same as those of the ring 20.

Figure 19:
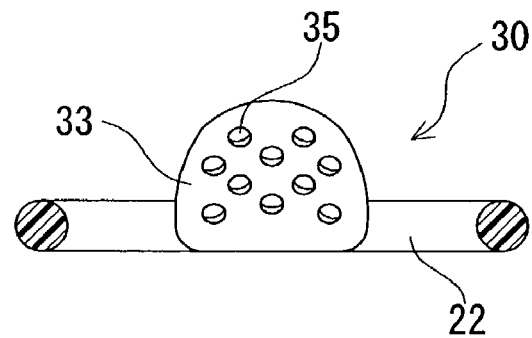
FIG. 19 is a sectional view taken along a line G—G of FIG. 18.
Figure 20:
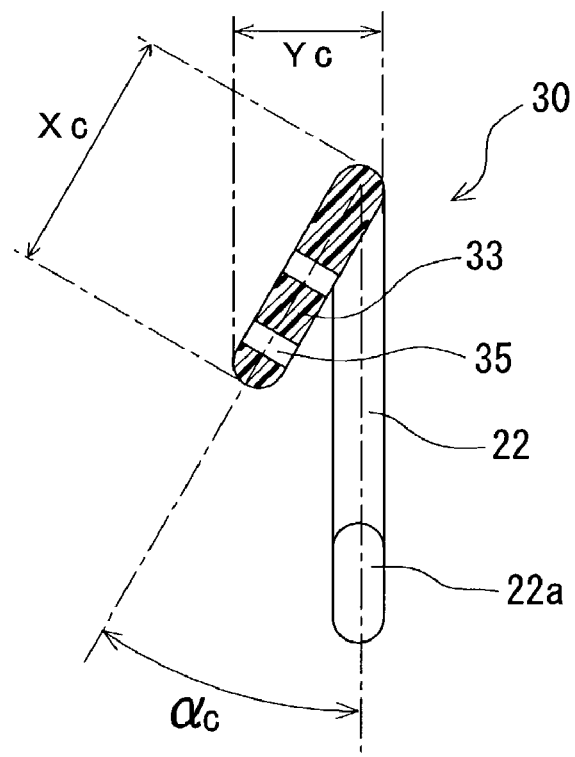
FIG. 20 is a sectional view taken along a line H—H of FIG. 18.

A ring 30, shown in FIGS. 18 through 20, for preventing a prolapse of the uterus and the urinary bladder according to another embodiment of the present invention will be described below.

Figure 18:
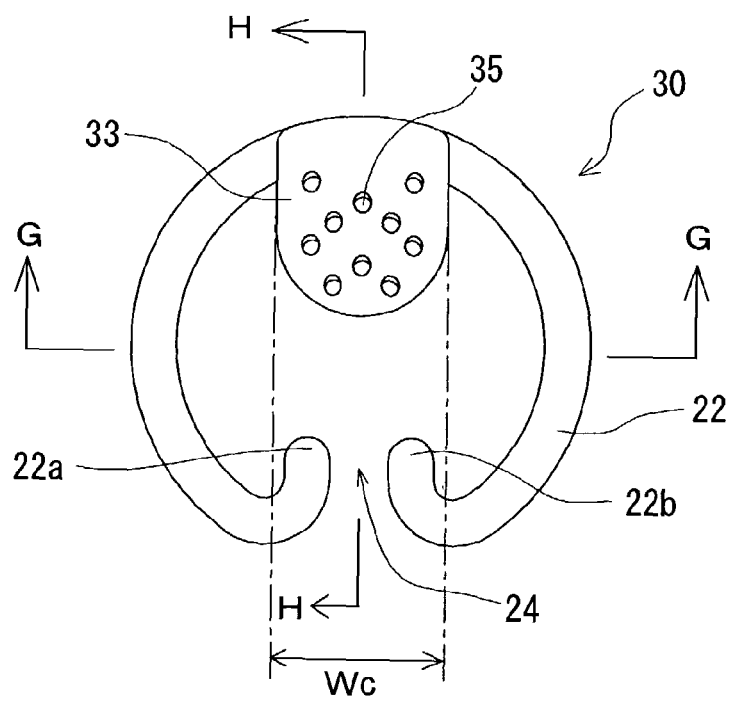
FIG. 18 is a front view showing a ring according to another embodiment of the present invention for preventing a prolapse of the uterus and the urinary bladder.

FIG. 18 is a front view showing the ring for preventing the prolapse of the uterus and the urinary bladder according to another embodiment of the present invention. FIG. 19 is a sectional view taken along a line G—G of FIG. 18. FIG. 20 is a sectional view taken along a line H—H of FIG. 18.

The specifications of the ring 30 are the same as those of the ring 20 except that the flexible flat plate part of the former is different from that of the latter.

A flexible flat plate part 33 is tongue-shaped in such a way that its one end is connected to the annular part 22. As shown in FIGS. 18 and 20, the flexible flat plate part 33 is so formed as to be disposed over a central region of an annular plane formed with the annular part 22. The length Xc of the flexible flat plate part shown in FIG. 20 is preferably in the range of 20 mm to 50 mm. The height Yc of the flexible flat plate part shown in FIG. 20 is preferably in the range of 20 mm to 40 mm. The angle ac formed between the flexible flat plate part and the annular part shown in FIG. 20 is favorably in the range of 30° to 150°. The width Wc of the flexible flat plate part shown in FIG. 18 is preferably in the range of 30 mm to 60 mm.

The flexible flat plate part 33 of the ring 30 of this embodiment is composed of a thick plate. Thus the flexible flat plate part 33 and the annular part 22 are integral with each other at the portion where the flexible flat plate part 33 is connected to the annular part 22. The flexible flat plate part 33 is chamfered and thus uncornered. The thickness of the flexible flat plate part 33 is preferably in the range of 3 mm to 8 mm. The leading end of the flexible flat plate part 33 is tongue-shaped or curved like a circular arc. The flexible flat plate part 33 has a plurality of openings 35 penetrating therethrough The opening 35 prevents an excessive contact between the flexible flat plate part 33 and the organism and prevents a metabolite from depositing between the flexible flat plate part 33 and the organism. The dimension (diameter) of the opening 35 is preferably in the range of 1 mm to 4 mm. The number of the openings 35 is preferably in the range of one to three/cm$^2$.

Figure 22:
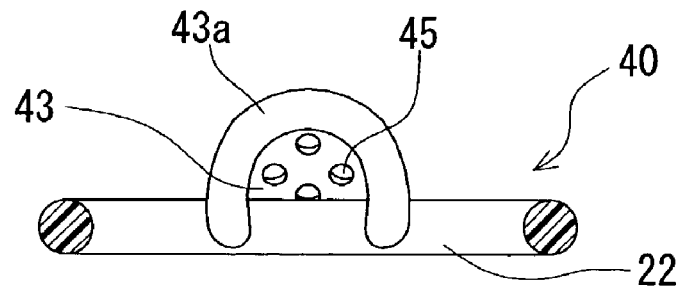
FIG. 22 is a sectional view taken along a line I—I of FIG. 21.
Figure 23:
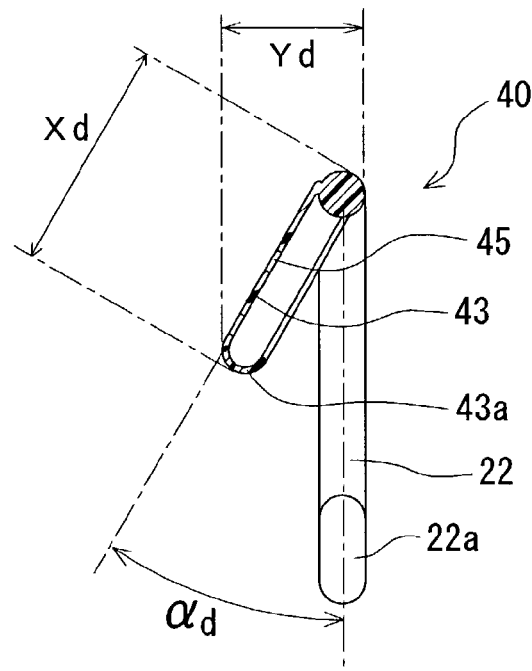
FIG. 23 is a sectional view taken along a line J—J of FIG. 21.

A ring 40, shown in FIGS. 21 through 23, for preventing a prolapse of the uterus and the urinary bladder according to another embodiment of the present invention will be described below.

Figure 21:
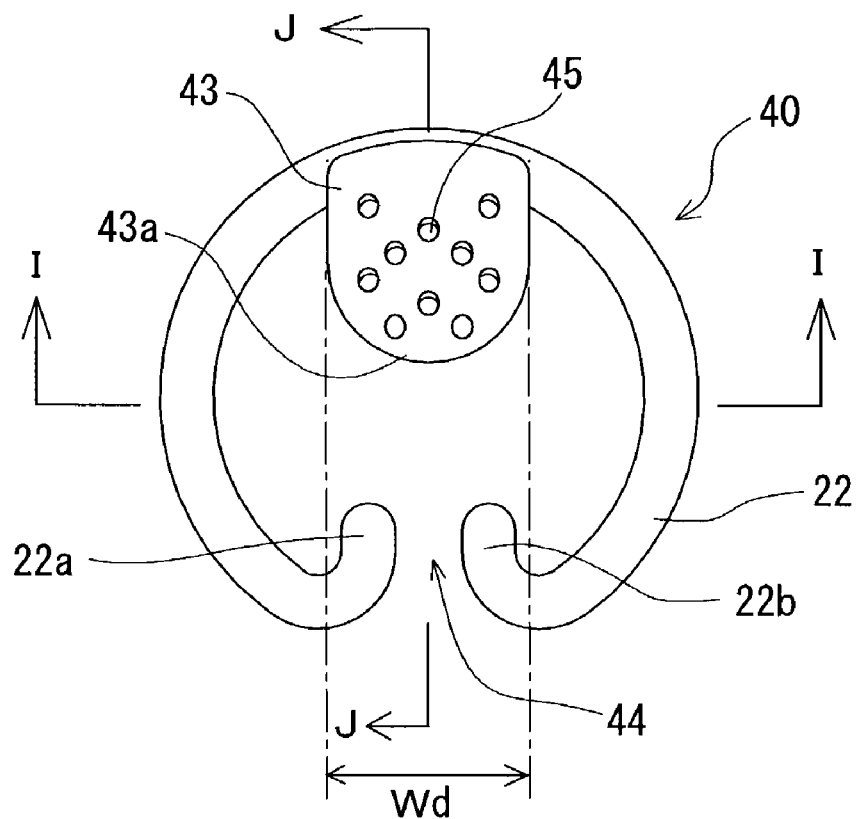
FIG. 21 is a front view showing a ring according to another embodiment of the present invention for preventing a prolapse of the uterus and the urinary bladder.

FIG. 21 is a front view showing the ring for preventing the prolapse of the uterus and the urinary bladder according to another embodiment of the present invention. FIG. 22 is a sectional view taken along a line I—I of FIG. 21. FIG. 23 is a sectional view taken along a line J—J of FIG. 21.

The specifications of the ring 40 are the same as those of the ring 20 except that the flexible flat plate part of the former is different from that of the latter.

A flexible flat plate part 43 is tongue-shaped in such a way that its one end is connected to the annular part 22. As shown in FIGS. 21 and 23, the flexible flat plate part 43 is so formed as to extend over a central region of an annular plane formed with the annular part 22. The length Xd of the flexible flat plate part shown in FIG. 23 is preferably in the range of 20 mm to 50 mm. The height Yd of the flexible flat plate part shown in FIG. 23 is preferably in the range of 20 mm to 40 mm. The angle αd formed between the flexible flat plate part and the annular part shown in FIG. 23 is favorably in the range of 30° to 150° and more favorably in the range of 30° to 60°. The width Wd of the flexible flat plate part shown in FIG. 21 is preferably in the range of 30 mm to 60 mm.

The flexible flat plate part 43 of the ring 40 of this embodiment is composed of a thin plate. The periphery of the flexible flat plate part 43 is curved toward the annular part 22 in such an extent that the end of the curved periphery faces toward the flexible flat plate part In other words, the periphery is curled. Therefore the end of the curved periphery of the flexible flat plate part hardly contacts an organism and thus hardly damages the organism.

The thickness of the flexible flat plate part is preferably in the range of 3 mm to 8 mm. The leading end of the flexible flat plate part 43 is tongue-shaped or curved like a circular arc. The flexible flat plate part 43 has a plurality of openings 45 penetrating therethrough The opening 45 prevents an excessive contact between the flexible flat plate part 43 and the organism and prevents a metabolite from depositing between the flexible flat plate part 43 and the organism. The dimension (diameter) of the opening 45 is preferably in the range of 1 mm to 4 mm. The number of the openings 45 is preferably in the range of one to three/cm$^2$.

A ring, shown in drawings, for preventing the prolapse of the uterus and the urinary bladder according to another embodiment of the present invention will be described below.

Figure 33:
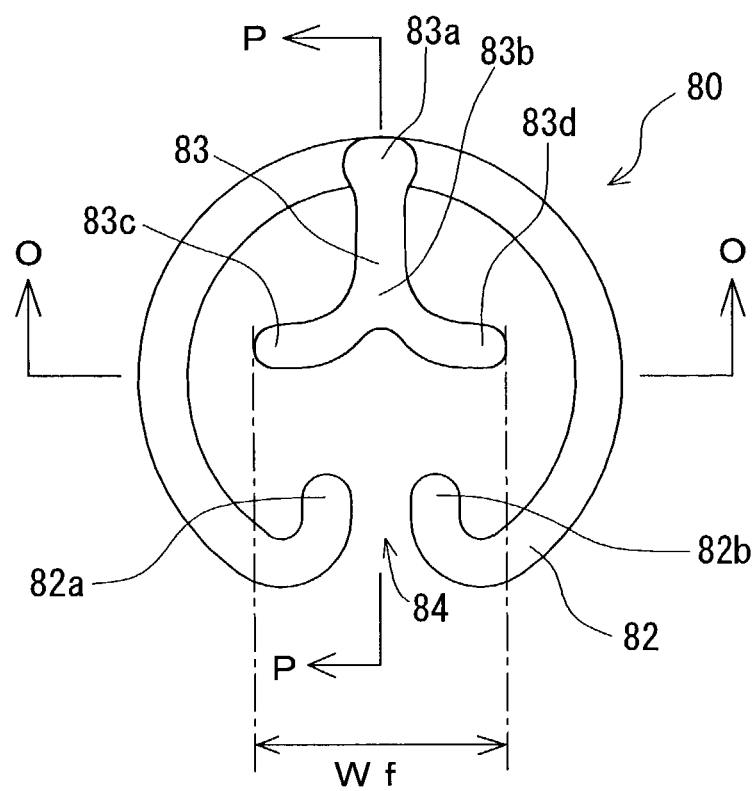
FIG. 33 is a front view showing a ring according to another embodiment of the present invention for preventing a prolapse of the uterus and the urinary bladder.
Figure 34:
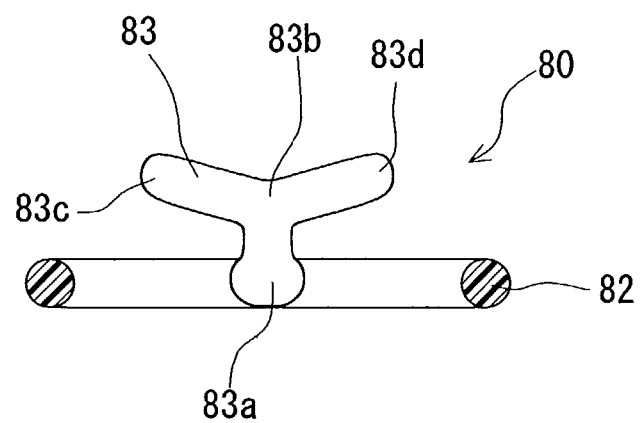
FIG. 34 is a sectional view taken along a line O—O of FIG. 33.
Figure 35:
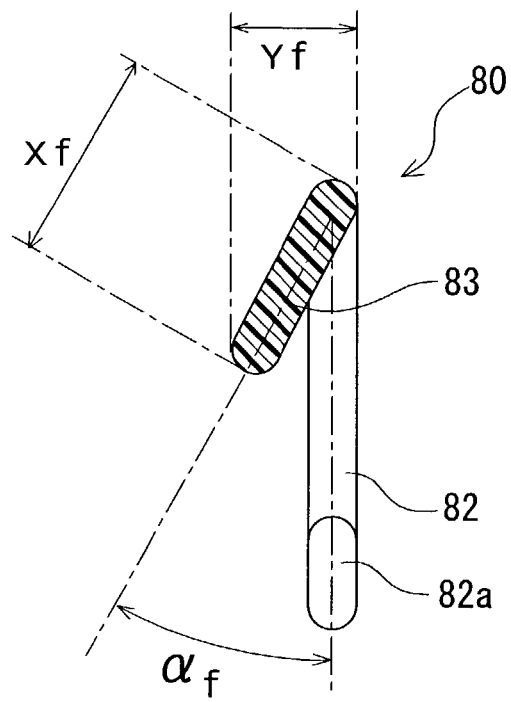
FIG. 35 is a sectional view taken along a line P—P of FIG. 33.

FIG. 33 is a front view showing the ring for preventing the prolapse of the uterus and the urinary bladder according to another embodiment of the present invention. FIG. 34 is a sectional view taken along a line O—O of FIG. 33. FIG. 35 is a sectional view taken along a line P—P of FIG. 33.

A ring 80 of the present invention for preventing the prolapse of the uterus and the urinary bladder has an annular part 82 and a flexible curved rod-shaped part 83 whose one end is connected to the annular part 82 and whose other end is divided into at least two branches in such a way that the other end is disposed over a central region of an annular plane formed with the annular part 82.

Similarly to the ring 1, the ring 80 of the embodiment has the annular part 82 for preventing the prolapse of the uterus, the flexible curved rod-shaped part 83 for preventing the prolapse of the urinary bladder, and an open portion 84, for preventing the prolapse of the rectum, formed by a partial absence of the annular part 82. Thus the ring 80 of the embodiment is of a type of preventing the prolapse of the uterus, the urinary bladder, and the rectum.

The ring 80 has the annular part 82 and the curved rod-shaped part 83 connected thereto.

The annular part 82 is approximately a circular annular body and has the open portion 84 formed by a partial absence of the annular part 82. The provision of the open portion 84 makes it easy to insert the ring 80 into an organism and remove it therefrom, prevents the prolapse of the rectum without causing a dyschezia, and prevents a rotation of the ring 80 in the organism. Ends 82a and 82b of the annular part 82 forming the open portion 84 are curved toward the inside of the annular part 82. Thus it is possible to prevent the ends 82a and 82b of the annular part 82 from directly contacting the organism, namely, the uterus. The configuration of the annular part 82 is not limited to a circle but may be an ellipse or a deformed circle. As shown in FIGS. 34 and 35, the annular part 82 is formed as a curved column having a circular cross section. The annular part 82 may be a chamfered and curved polygonal pillar or a curved elliptical pillar. Although the size of the annular part 82 is varied according to the constitution of a patient, it is preferable that the annular part 82 has a diameter in the range of 40 mm to 120 mm. The thickness (diameter) of the entire annular part 82 does not necessarily have to be uniform. For example, a portion of the annular part 82 confronting the open portion 84 may be narrower than other portions thereof. This configuration allows an easier deformation of the annular part 82.

The thickness, or the diameter (maximum diameter) of the pillar constituting the annular part is preferably in the range of 4 mm to 12 mm. The dimension of the open portion 84, namely, the dimension of the circular arc corresponding to the absent portion of the annular part 82 is favorably in the range of 1/5 to 1/30 of the circumference of the annular part 82 and more favorably in the range of 1/8 to 1/20 thereof. In the embodiment shown in FIG. 33 in which the ring 80 has the open portion 84, the distance between the ends 82a and 82b of the annular part 82 is preferably in the range of 10 to 30 mm. It is preferable that the ends 82a and 82b of the annular part 82 are curved toward the inside of the annular part 82 and approximately parallel with each other.

The curved rod-shaped part 83 is inverted Y-shaped in such a way that one end 83a thereof is connected to the annular part 82 and the other end thereof forks into two branches formed as free ends 83*c* and 83*d*. As shown in FIGS. 33 and 35, the central portion of the bifurcated free ends 83*c* and 83*d*, namely, a branch portion 83*b* is so formed as to be disposed over a central region of an annular plane formed with the annular part 82. The length Xf of the curved rod-shaped part shown in FIG. 35 is preferably in the range of 20 mm to 50 mm. The height Yf of the curved rod-shaped part shown in FIG. 35 is preferably in the range of 20 mm to 40 mm. The angle αf formed between the curved rod-shaped part and the annular part shown in FIG. 35 is favorably in the range of 30° to 150° and more favorably in the range of 30° to 60°. The width Wf of the curved rod-shaped part shown in FIG. 33 is preferably in the range of 30 mm to 60 mm.

As shown in FIGS. 33 through 35, the curved rod-shaped part 83 is formed as a curved column having a circular cross section. The curved rod-shaped part 83 may be a chamfered and curved polygonal pillar or a curved elliptical pillar. It is preferable that the pillar constituting the curved rod-shaped part 83 has a diameter (maximum diameter) of 4 mm to 12 mm. The thickness (diameter) of the entire curved rod-shaped part 83 does not necessarily have to be uniform. For example, the branch portion 83*b* may be thicker than other portions thereof. In the embodiment shown in FIGS. 33 through 35, the one end 83*a* of the curved rod-shaped part 83 is formed thicker than the other portions thereof to increase the strength of connection between the one end 83*a* and the annular part 82. The leading end of each of the bifurcated free ends 83*c* and 83*d* is rounded like a hemisphere.

The entire ring 80 of the embodiment is formed of a material flexible in some extent It is preferable that the material for the curved rod-shaped part 83 is more flexible than the material for the annular part 82.

As the material for the ring, those for the ring 1 can be preferably used. Of these materials, it is particularly preferable to use the thermoplastic material. A resin that softens at a low temperature in the range of 50° C. to 100° C. is particularly preferable. The entire ring may be formed of the resin having a low softening point But it is indispensable that the annular part 82 is formed of the resin having a low softening point By using the resin having a low softening point and heating it to the above-described temperature, the annular part can be deformed into a configuration suitable for the configuration of the portion of a patient into which the ring is inserted. A deformed configuration can be maintained by cooling the resin. By doing so, it is possible to make removal of the ring from the inserted portion of the organism rare and reduce the degree of an unpleasant feeling of physical disorder at the time of its insertion into the organism. By using the resin having a low softening point and heating it to the above-described temperature, it is possible to arbitrarily alter the angle of the curved rod-shaped part with respect to the annular part as necessary.

The material for the annular part and the material for the curved rod-shaped part may be differentiated from each other. More specifically, the semirigid material may be used for the annular part and the flexible material may be used for the curved rod-shaped part In this case, both may be joined to each other with an adhesive agent but it is preferable to integrate both with each other by carrying out a two-color molding method. As a combination of the materials when the two-color molding method is carried out, it is preferable that both are highly compatible with each other. More specifically, it is conceivable to select polyolefin as the semirigid material and polyolefin elastomer as the flexible material, ester resin as the semirigid material and polyester elastomer as the flexible material or styrene resin as the semirigid material and styrene elastomer as the flexible material.

Figure 36:
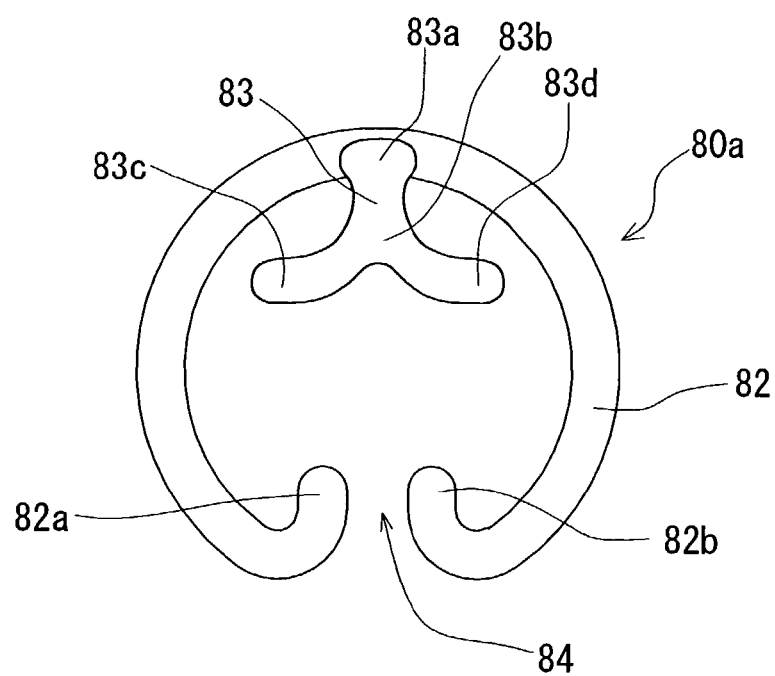
FIG. 36 is a front view showing a ring according to another embodiment of the present invention for preventing a prolapse of the uterus and the urinary bladder.

Like a ring 80*a* shown in FIG. 36, the curved rod-shaped part 83 may be shorter than that of the ring 80 shown in FIGS. 33 through 35. In this case, with reference to FIG. 35, the length Xf of the curved rod-shaped part is preferably in the range of 20 mm to 50 mm. The height Yf of the curved rod-shaped part is preferably in the range of 20 mm to 40 mm. The other specifications of the ring 80*a* are the same as those of the ring 80.

Figure 37:
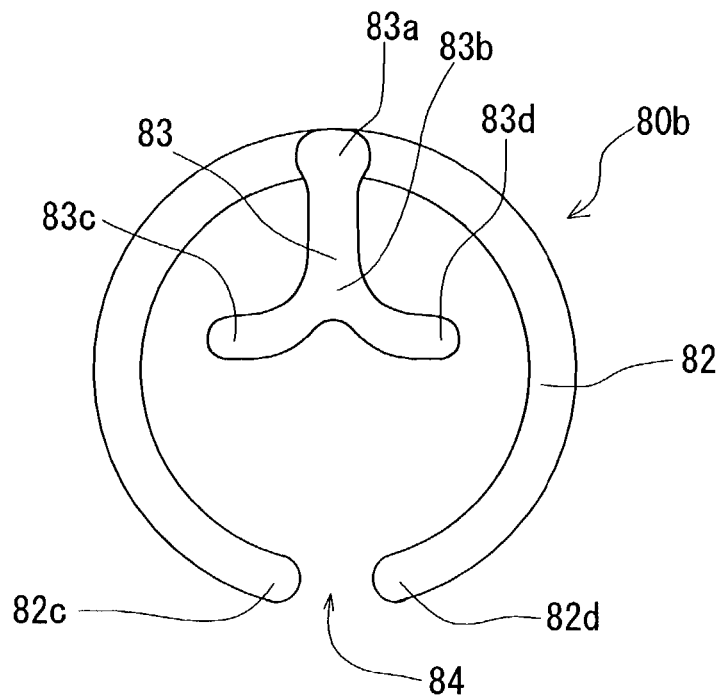
FIG. 37 is a front view showing a ring according to another embodiment of the present invention for preventing a prolapse of the uterus and the urinary bladder.

Like a ring 80*b* shown in FIG. 37, ends 82*c* and 82*d* of the annular part 82 at its open portion may confront each other. In the ring 80*b*, the dimension of the open portion 84, namely, the dimension of the circular arc corresponding to the absent portion of the annular part 82 is favorably in the range of ⅕ to ¹⁄₃₀ of the circumference of the annular part 82 and more favorably in the range of ⅛ to ½₀ thereof. The distance between the ends 82*c* and 82*d* of the annular part 82 is preferably in the range of 10 mm to 30 mm. The other specifications of the ring 80*b* are the same as those of the ring 80 shown in FIGS. 33 through 35.

Figure 38:
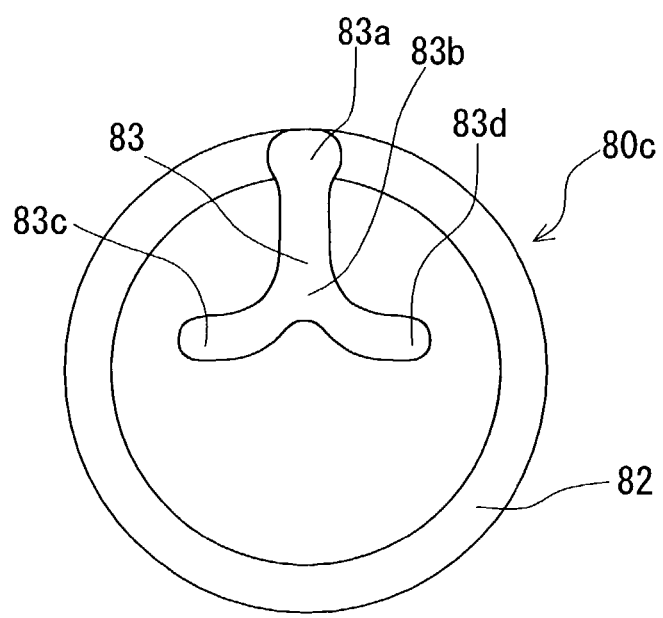
FIG. 38 is a front view showing a ring according to another embodiment of the present invention for preventing a prolapse of the uterus and the urinary bladder.

Like a ring 80*c* shown in FIG. 38, the annular part 82 may not be provided with the open portion. The ring 80*c* is effective for a patient having the symptoms of the prolapse of the uterus and the urinary bladder but not the symptoms of the rectum. The other specifications of the ring 80*c* are the same as those of the ring 80 shown in FIGS. 33 through 35.

A ring, shown in drawings, for preventing a prolapse of the uterus and the urinary bladder according to another embodiment of the present invention will be described below.

A ring 90 of the present invention for preventing the prolapse of the uterus and the urinary bladder has an annular part 92 and a flexible curved rod-shaped part 93 that is connected to the annular part 92 at a portion 93*b* thereof where one and other ends thereof are integrated with each other and so formed as to be connected to the annular part 92 and whose intermediate portion 93*a* interposed between the one end thereof and the other end thereof is so formed as to be disposed over a central region of an annular plane formed with the annular part 92.

Figure 39:
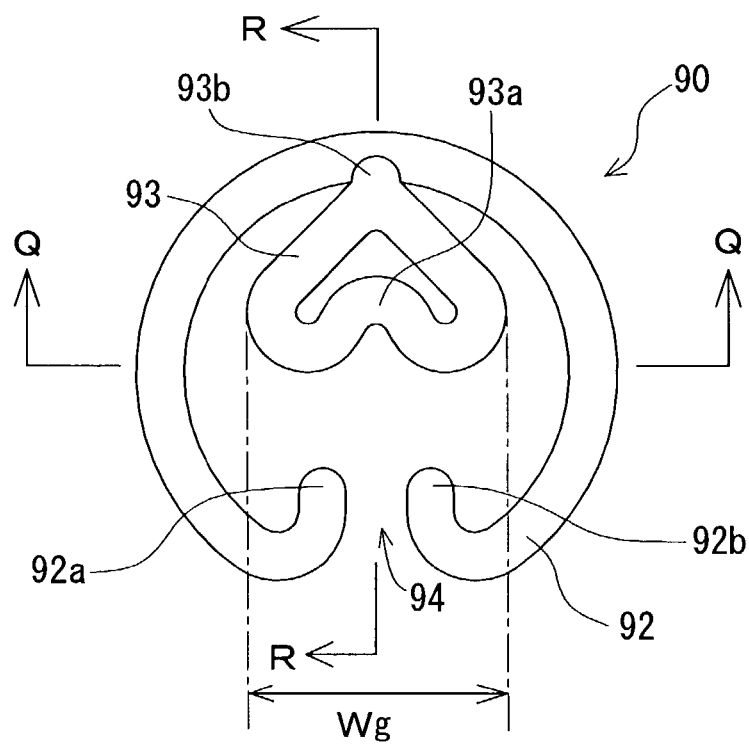
FIG. 39 is a front view showing a ring according to another embodiment of the present invention for preventing a prolapse of the uterus and the urinary bladder.
Figure 40:
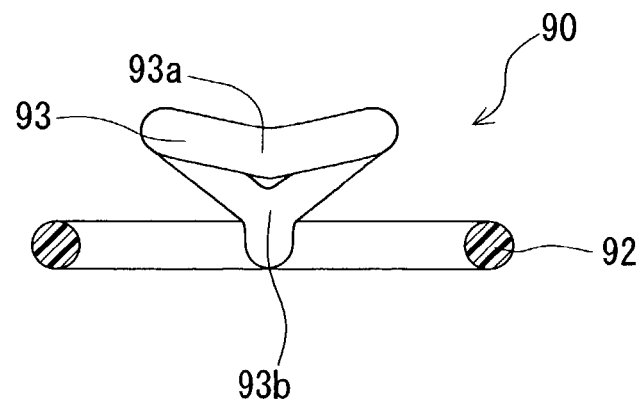
FIG. 40 is a sectional view taken along a line Q—Q of FIG. 39.
Figure 41:
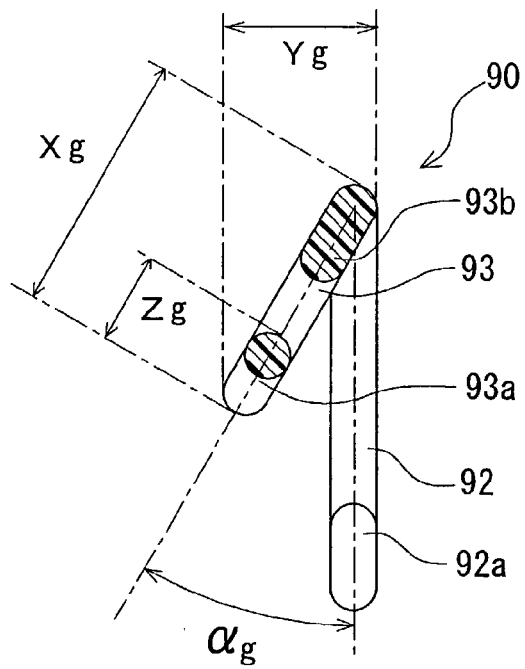
FIG. 41 is a sectional view taken along a line R—R of FIG. 39.
Figure 42:
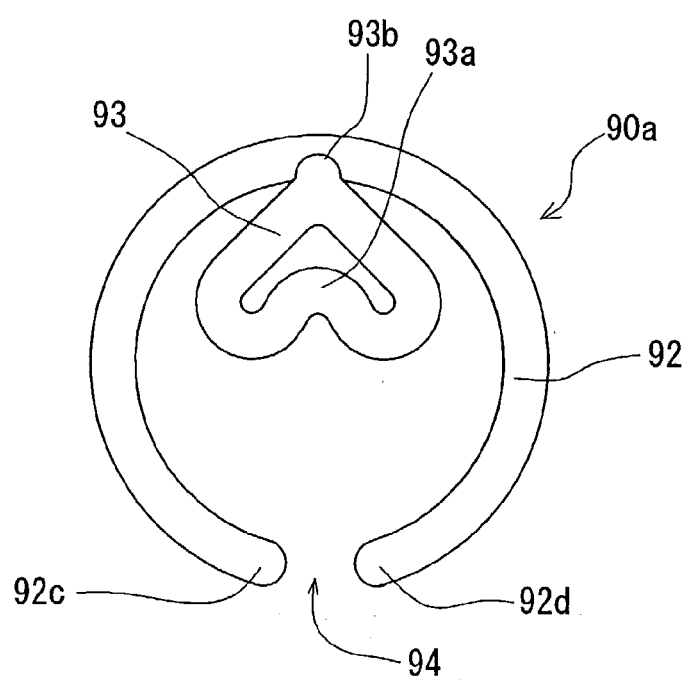
FIG. 42 is a front view showing a ring according to another embodiment of the present invention for preventing a prolapse of the uterus and the urinary bladder.
Figure 43:
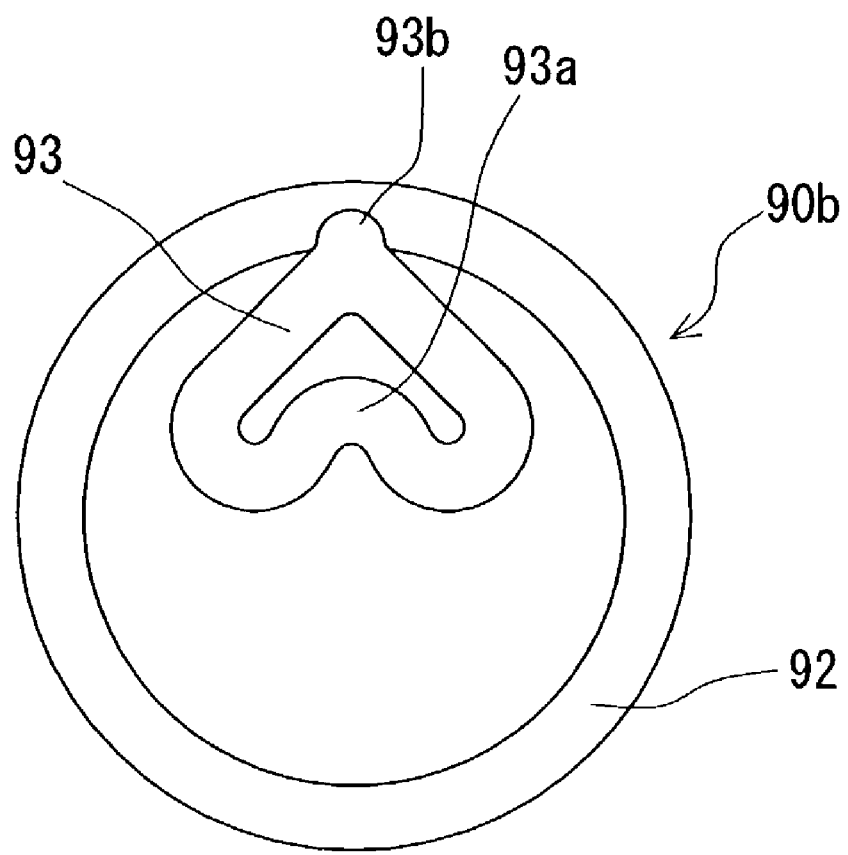
FIG. 43 is a front view showing a ring according to another embodiment of the present invention for preventing a prolapse of the uterus and the urinary bladder.

FIG. 39 is a front view showing a ring for preventing the prolapse of the uterus and the urinary bladder according to another embodiment of the present invention. FIG. 40 is a sectional view taken along a line Q—Q of FIG. 39. FIG. 41 is a sectional view taken along a line R—R of FIG. 39. FIG. 42 is a front view showing a ring for preventing a prolapse of the uterus and the urinary bladder according to another embodiment of the present invention. FIG. 43 is a front view showing a ring for preventing a prolapse of the uterus and the urinary bladder according to another embodiment of the present invention.

Similarly to the ring 1, the ring 90 of the embodiment has the annular part 92 for preventing the prolapse of the uterus, the flexible curved rod-shaped part 93 for preventing the prolapse of the urinary bladder, and an open portion 94, for preventing the prolapse of the rectum, formed by a partial absence of the annular part 92. Thus the ring 90 of the embodiment is of a type of preventing the prolapse of the uterus, the urinary bladder, and the rectum.

The ring 90 has the annular part 92 and the curved rod-shaped part 93 connected thereto.

The annular part 92 is approximately a circular annular body and has the open portion 94 formed by a partial absence of the annular part 92. The provision of the open portion 94 makes it easy to insert the ring 90 into an organism and remove it therefrom, prevents the prolapse of the rectum without causing a dyschezia, and prevents a rotation of the ring 90 in the organism. Ends 92a and 92b of the annular part 92 forming the open portion 94 are curved toward the inside of the annular part 92. Thus it is possible to prevent the ends 92a and 92b of the annular part 92 from directly contacting a organism, namely, the uterus. The configuration of the annular part 92 is not limited to a circle but may be an ellipse or a deformed circle. As shown in FIGS. 40 and 41, the annular part 92 is formed as a curved column having a circular cross section. The annular part 92 may be a chamfered and curved polygonal pillar or a curved elliptical pillar. Although the size of the annular part 92 is varied according to the constitution of a patient, it is preferable that the annular part 92 has a diameter in the range of 40 to 120 mm. The thickness (diameter) of the entire annular part 92 does not necessarily have to be uniform. For example, a portion of the annular part 92 confronting the open portion 94 may be narrower than other portions thereof. This configuration allows an easier deformation of the annular part 92.

The thickness, or the diameter (maximum diameter) of the pillar constituting the annular part is preferably in the range of 4 mm to 12 mm. The dimension of the open portion 94, namely, the dimension of the circular arc corresponding to the absent portion of the annular part 92 is favorably in the range of 1/5 to 1/30 of the circumference of the annular part 92 and more favorably in the range of 1/8 to 1/20 thereof. In the embodiment shown in FIG. 39 in which the ring 90 has the open portion 94, the distance between the ends 92a and 92b of the annular part 92 is preferably in the range of 10 mm to 30 mm. It is preferable that the ends 92a and 92b of the annular part 92 are curved toward the inside of the annular part 92 and approximately parallel with each other.

The curved rod-shaped part 93 is an inverted heart-shaped in such a way that an integral portion 93b thereof where one and other ends thereof are integrated with each other is connected to the annular part 92. As shown in FIGS. 39 and 41, a central portion 93a of the curved rod-shaped part 93 is so formed as to be disposed over a central region of an annular plane formed with the annular part 92. The length Xg of the curved rod-shaped part shown in FIG. 41 is preferably in the range of 20 mm to 50 mm. The height Yg of the curved rod-shaped part shown in FIG. 41 is preferably in the range of 20 mm to 40 mm. The angle αg formed between the curved rod-shaped part and the annular part shown in FIG. 41 is favorably in the range of 30° to 150° and more favorably in the range of 30° to 60°. The width Wg of the curved rod-shaped part 93 shown in FIG. 39 is preferably in the range of 30 mm to 60 mm.

As shown in FIGS. 39 through 41, the curved rod-shaped part 93 is formed as a curved column having a circular cross section. The curved rod-shaped part 93 may be a chamfered and curved polygonal pillar or a curved elliptical pillar. It is preferable that the pillar constituting the curved rod-shaped part 93 has a diameter (maximum diameter) of 4 mm to 12 mm. The thickness (diameter) of the entire curved rod-shaped part 93 does not necessarily have to be uniform. For example, a central portion 93a of the curved rod-shaped part 93 may be thicker than other portions thereof. To increase the strength of connection between the integral portion 93b of the curved rod-shaped part 93 and the annular part 92, the integral portion 93b may be thicker than other portions thereof.

The entire ring 90 of the embodiment is formed of a material flexible in some extent It is preferable that the material for the curved rod-shaped part 93 is more flexible than the material for the annular part 92.

As the material for the ring, those for the ring 1 can be preferably used. Of these materials, it is particularly preferable to use the thermoplastic material. A resin that softens at a low temperature in the range of 50° C. to 100° C. is particularly preferable. The entire ring may be formed of the resin having a low softening point But it is indispensable that the annular part 92 is formed of the resin having a low softening point By using the resin having a low softening point and heating it to the above-described temperature, the annular part can be deformed into a configuration suitable for the configuration of the portion of a patient into which the ring is inserted. A deformed configuration can be maintained by cooling the resin. By doing so, it is possible to make removal of the ring from the inserted portion of the organism rare and reduce the degree of an unpleasant feeling of physical disorder at the time of its insertion into the organism. By using the resin having a low softening point and heating it to the above-described temperature, it is possible to arbitrarily alter the angle of the curved rod-shaped part with respect to the annular part as necessary.

The material for the annular part and the material for the curved rod-shaped part may be differentiated from each other. More specifically, the semirigid material may be used for the annular part and the flexible material may be used for the curved rod-shaped part In this case, both may be joined to each other with an adhesive agent, but it is preferable to integrate both by carrying out a two-color molding method. As a combination of the materials when the two-color molding method is carried out, it is preferable that both are highly compatible with each other. More specifically, it is conceivable to select polyolefin as the semirigid material and polyolefin elastomer as the flexible material, ester resin as the semirigid material and polyester elastomer as the flexible material, and styrene resin as the semirigid material and styrene elastomer as the flexible material.

Like a ring 90a shown in FIG. 42, ends 92c and 92d of the annular part 92 at its open portion may confront each other. In the ring 90a, the dimension of the open portion 94, namely, the dimension of the circular arc corresponding to the absent portion of the annular part 92 is favorably in the range of 1/5 to 1/30 of the circumference of the annular part 92 and more favorably in the range of 1/8 to 1/20 thereof. The distance between the ends 92c and 92d of the annular part 92 is preferably in the range of 10 mm to 30 mm. Other specifications of the ring 90a are the same as those of the ring 90 shown in FIGS. 39 through 41.

Like a ring 90b shown in FIG. 43, the annular part 92 may not be provided with the open portion. The ring 90b is effective for a patient having the symptoms of the prolapse of the uterus and the urinary bladder but not the symptoms of the rectum. The other specifications of the ring 90b are the same as those of the ring 1 shown in FIGS. 1 through 3.

A ring, of the present invention, for preventing the prolapse of the uterus and the rectum will be described below.

Figure 24:
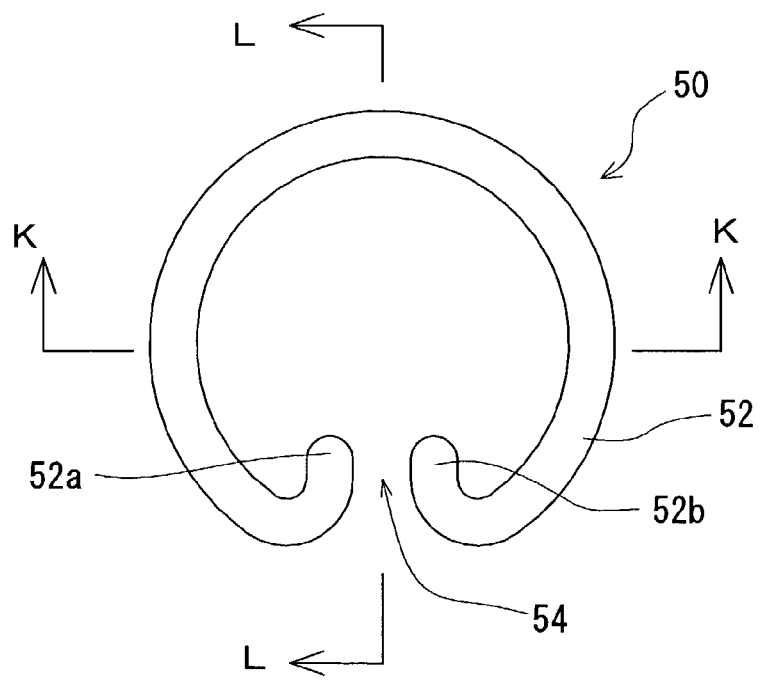
FIG. 24 is a front view showing a ring according to another embodiment of the present invention for preventing a prolapse of the uterus and the urinary bladder.
Figure 25:
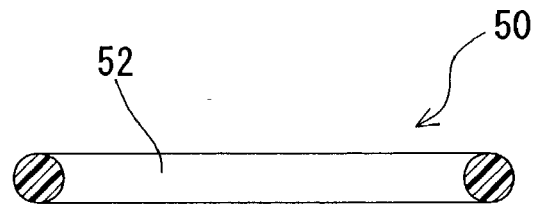
FIG. 25 is a sectional view taken along a line K—K of FIG. 24.
Figure 26:
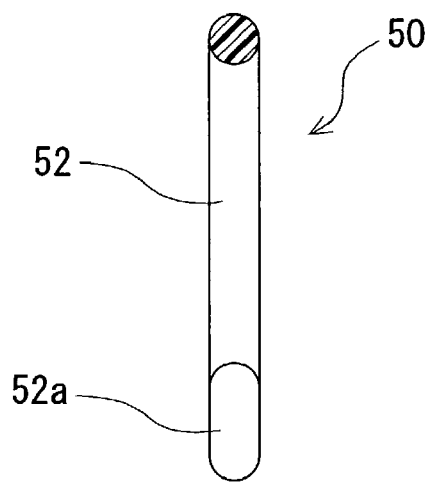
FIG. 26 is a sectional view taken along a line L—L of FIG. 24.

FIG. 24 is a front view showing a ring for preventing a prolapse of the uterus and the rectum according to another embodiment of the present invention. FIG. 25 is a sectional view taken along a line K—K of FIG. 24. FIG. 26 is a sectional view taken along a line L—L of FIG. 24

A ring 50 of the present invention for preventing the prolapse of the uterus and the rectum is formed of a flexible annular member 52 having an open portion 54 formed owing to a partial absence thereof. Both ends 52a and 52b of the annular member 52 forming the open portion 54 are curved toward the inside of the annular part 52.

The annular member 52 is approximately a circular annular body and has the open portion 54 formed by a partial absence of the annular member 52. The provision of the open portion 54 makes it easy to insert the ring 50 into an organism and remove it therefrom, prevents the prolapse of the rectum without causing a dyschezia, and prevents a rotation of the ring 50 in the organism. Ends 52a and 52b of the annular member 52 forming the open portion 54 are curved toward the inside of the annular member 52. Thus it is possible to prevent the ends 52a and 52b of the annular member 52 from directly contacting the organism, namely, the uterus. The configuration of the annular member 52 is not limited to a circle but may be an ellipse or a deformed circle. As shown in FIGS. 25 and 26, the annular member 52 is formed as a curved column having a circular cross section. The annular member 52 may be a chamfered and curved polygonal pillar or a curved elliptical pillar. Although the size of the annular member 52 is varied according to the constitution of a patient, it is preferable that the annular member 52 has a diameter in the range of 40 mm to 120 mm. The thickness of the pillar composing the annular member 52 is preferably in the range of 4 mm to 12 mm. The thickness (diameter) of the entire annular member 52 does not necessarily have to be uniform. For example, a portion of the annular member 52 confronting the open portion 54 may be narrower than other portions thereof. This configuration allows an easier deformation of the annular member 52.

The dimension of the open portion 54, namely, the dimension of the circular arc corresponding to the absent portion of the member 52 is favorably in the range of ⅕ to 1/30 of the circumference of the annular member 52 and more favorably in the range of ⅛ to 1/20 thereof. The distance between the ends 52a and 52b of the annular member 52 is preferably in the range of 10 mm to 30 mm. It is preferable that the ends 52a and 52b of the annular member 52 are curved toward the inside of the annular member 52 and approximately parallel with each other.

The entire ring 50 of the embodiment is formed of a material flexible in some extent.

As the material for the ring, the following substances can be used: semirigid materials such as polycarbonate, acrylic resin (for example, polyacrylate, polymethyl methacrylate, polyacrylamide, acrylonitrile-styrene copolymer, acrylonitrile-butadiene-styrene copolymer, polyester (for example, polyethylene terephthalate, polybutylene terephthalate), polyolefin (for example, polyethylene, polypropylene, ethylene-propylene copolymer, ethylene-vinyl acetate copolymer, mixture of polypropylene and polyethylene or polybutene), styrene resin (for example, polystyrene, methacrylate-styrene copolymer, methacrylate-butylene-styrene copolymer), polyamide (for example, 6 nylon, 66 nylon), and polysulfone; flexible materials such as synthetic rubber such as urethane rubber, silicone rubber, and butadiene rubber, natural rubber such as latex rubber, and thermoplastic materials such as olefin elastomer (for example, polyethylene elastomer, polypropylene elastomer), amide elastomer (for example, polyamide elastomer), styrene elastomer (for example, styrene-butadiene-styrene copolymer, styrene-isoprene-styrene copolymer, styrene-ethylene-butylene-styrene copolymer), polyurethane (for example, polyester polyurethane, polyether polyurethane), and urethane elastomer (for example, thermoplastic polyurethane, for example, thermoplastic polyether polyurethane and thermoplastic polyester polyurethane). Of these materials, it is preferable to use the thermoplastic materials. A resin that softens at a low temperature in the range of 50° C. to 100° C. is particularly preferable. By using the resin having a low softening point and heating it to the above-described temperature, the annular member (annular member) can be deformed into a configuration suitable for the configuration of the portion of a patient into which the ring is inserted. A deformed configuration can be maintained by cooling the resin. By doing so, it is possible to make removal of the ring from the inserted portion of the organism rare and reduce the degree of an unpleasant feeling of physical disorder at the time of its insertion into the organism.

The operation of the ring 50 is described below.

Similarly to the ring 1 shown in FIG. 44, the ring 50 is used by being inserted into a vagina 61. As shown in FIG. 44, the annular member 52 is inserted obliquely into the vagina 61 in such a way that the open portion of the annular member 52 is disposed at a deep portion of the uterus 62 and that the lower portion of the vagina is penetrated a little into the open portion. In this state, the uterus 62 is pressed upward by the annular member 52, and the rectal wall 64 is pressed upward by the annular member 52 through the vaginal wall. Thereby the symptoms of the prolapse of the uterus, the urinary bladder, and the rectum are softened. Since the annular member 52 has the open portion, i.e., since it has a portion that does not press the rectum, it is possible to reduce occurrence of dyschezia.

The ring of the present invention for preventing a prolapse of the uterus and the urinary bladder has an annular part and a flexible curved rod-shaped part whose one end and other end are so formed as to be connected to the annular part and whose intermediate portion interposed between the one end and the other end is so formed as to be disposed over a central region of an annular plane formed with the annular part.

Owing to this construction, the ring is inserted obliquely into the vagina in such a way that one end of the ring is disposed at the deep portion of the uterus and that the lower portion of the urinary bladder is disposed on the curved rod-shaped part Thereby the uterus is pressed upward by the annular part, and the urinary bladder can be supported by the curved rod-shaped part from below. Thus the symptoms of the prolapse of the uterus and the urinary bladder can be reduced without performing a surgical invasion.

The ring of the present invention for preventing a prolapse of the uterus and the urinary bladder having an annular part, and a flexible curved rod-shaped part whose one end and other end integral with the one end are so formed as to be connected to the annular part and whose intermediate portion interposed between the one end and the other end is so formed as to be disposed over a central region of an annular plane formed with the annular part.

Owing to this construction, the ring is inserted obliquely into the vagina in such a way that one end of the ring is disposed at the deep portion of the uterus and that the lower portion of the urinary bladder is disposed on the curved rod-shaped part Thereby the uterus is pressed upward by the annular part, and the urinary bladder can be supported by the curved rod-shaped part from below. Thus the symptoms of the prolapse of the uterus and the urinary bladder can be softened without performing a surgical invasion.

The ring of the present invention for preventing a prolapse of the uterus and the urinary bladder having an annular part, and a flexible curved rod-shaped part whose one end is connected to the annular part and whose other end is divided into at least two branches in such a way that said other end is disposed over a central region of an annular plane formed with the annular part.

Owing to this construction, the ring is inserted obliquely into the vagina in such a way that one end of the ring is disposed at the deep portion of the uterus and that the lower portion of the urinary bladder is disposed on the curved rod-shaped part Thereby the uterus is pressed upward by the annular part, and the urinary bladder can be supported by the curved rod-shaped part from below. Thus the symptoms of the prolapse of the uterus and the urinary bladder can be softened without performing a surgical invasion.

The ring of the present invention for preventing a prolapse of the uterus and the urinary bladder has an annular part; and a tongue-shaped flexible flat plate part formed on said annular part in such a way that said flexible flat plate part is disposed over a central region of an annular plane formed with said annular part.

Owing to this construction, the ring is inserted obliquely into the vagina in such a way that one end of the ring is disposed at the deep portion of the uterus and that the lower portion of the urinary bladder is disposed on the curved rod-shaped part Thereby the uterus is pressed upward by the annular part, and the urinary bladder can be supported by the curved rod-shaped part from below. Thus the symptoms of the prolapse of the uterus and the urinary bladder can be softened without performing a surgical invasion.

The ring of the present invention for preventing a prolapse of the uterus and the rectum having a flexible annular member having an open portion formed by a partial absence thereof. Both ends of the annular member forming the open portion are curved toward an inside of the annular member.

Owing to this construction, by inserting the ring obliquely into the vagina, with the open portion of the annular member disposed at the deep portion of the uterus and with the lower portion of the vagina penetrating a little into the open portion. Thereby the uterus is pressed upward by the annular member, and the rectal wall is pressed upward by the annular member through the vaginal wall. Therefore the symptoms of the prolapse of the uterus and the urinary bladder can be reduced without performing a surgical invasion. Since the annular member has the open portion, i.e., since it has a portion that does not press the rectum, it is possible to reduce occurrence of dyschezia.

What is claimed is:

1. A ring for preventing a prolapse of the uterus and the urinary bladder comprising:
   an annular part;
   a flexible curved rod-shaped part whose one end and other end are so formed as to be connected to said annular parts,
   an intermediate portion of said flexible curved rod-shaped part is interposed between said one end and said other end and is so formed as to be disposed over a central region of an annular plane formed with said annular part, and
   a central portion of said intermediate portion of said flexible curved rod-shaped part is curved toward an intermediate area between the one end of said flexible curved rod-shaped part and the other end of said flexible curved rod-shaped part.

2. A ring for preventing a prolapse of the uterus and the urinary bladder comprising:
   an annular part;
   a flexible curved rod-shaped part whose one end and other end integral with said one end are so formed as to be connected to said annular part,
   an intermediate portion of said flexible curved rod-shaped part is interposed between said one end and said other end and is so formed as to be disposed over a central region of an annular plane formed with said annular part, and
   a central portion of said intermediate portion of said flexible curved rod-shaped part is curved toward an intermediate area between the one end of said flexible curved rod-shaped part and the other end of said flexible curved rod-shaped part.

3. A ring according to claim 1, wherein said annular part is formed of a resin, having a low softening point, that softens at a temperature in a range of 50° C. to 100° C.

4. A ring according to claim 1, wherein said annular part has an open portion formed by a partial absence thereof.

5. A ring according to claim 4, wherein an end of said annular part forming said open portion is curved toward an inside of said annular part.

6. A ring according to claim 4, wherein said flexible curved rod-shaped part and said open part are formed at positions confronting each other.

7. A ring according to claim 2, wherein said annular part is formed of a resin, having a low softening point, that softens at a temperature in a range of 50° C. to 100 °C.

8. A ring according to claim 2, wherein said annular part has an open portion defined between two terminal end portions.

9. A ring according to claim 8, wherein at least one of said terminal end portions of said annular part forming said open portion is curved toward an inside of said annular part.

* * * * *